US011383019B2

(12) United States Patent
Carroll et al.

(10) Patent No.: US 11,383,019 B2
(45) Date of Patent: Jul. 12, 2022

(54) WOUND VIEW DRESSING AND CUSTOMIZATION KIT

(71) Applicant: KCI LICENSING, INC., San Antonio, TX (US)

(72) Inventors: Christopher A. Carroll, San Antonio, TX (US); Justin A. Long, Bournemouth (GB); Justin Rice, San Antonio, TX (US); Christopher B. Locke, Bournemouth (GB); Timothy M. Robinson, Blandford Forum (GB)

(*) Notice: Subject to any disclaimer, the term of this patent is extended or adjusted under 35 U.S.C. 154(b) by 163 days.

(21) Appl. No.: 16/513,266

(22) Filed: Jul. 16, 2019

(65) Prior Publication Data

US 2020/0023106 A1     Jan. 23, 2020

Related U.S. Application Data

(60) Provisional application No. 62/699,888, filed on Jul. 18, 2018.

(51) Int. Cl.
*A61F 13/00* (2006.01)
*A61M 1/00* (2006.01)
*A61F 13/02* (2006.01)

(52) U.S. Cl.
CPC ......... *A61M 1/90* (2021.05); *A61F 13/00063* (2013.01); *A61F 13/0206* (2013.01); *A61F 13/0216* (2013.01); *A61F 13/0243* (2013.01)

(58) Field of Classification Search
CPC ............ A61M 1/0088; A61F 13/00063; A61F 13/0206; A61F 13/0216; A61F 13/0243; A61F 13/022; A61F 13/00068
See application file for complete search history.

(56) References Cited

U.S. PATENT DOCUMENTS

| 1,355,846 | A | 10/1920 | Rannells |
| 2,547,758 | A | 4/1951 | Keeling |
| 2,632,443 | A | 3/1953 | Lesher |

(Continued)

FOREIGN PATENT DOCUMENTS

| AU | 550575 B2 | 3/1986 |
| AU | 745271 B2 | 3/2002 |

(Continued)

OTHER PUBLICATIONS

"A randomised controlled trial of the clinical effectiveness of multi-layer silicone foam dressings for the prevention of pressure injuries in high-risk aged care residents: The Border III Trial", Santamaria Nick et al., first published Apr. 10, 2018, International Wound Journal, vol. 15, Issue 3. (Year: 2018).*

(Continued)

*Primary Examiner* — Philip R Wiest
*Assistant Examiner* — Gregory J Feulner

(57) ABSTRACT

A dressing includes a foam layer, a plurality of cores extending substantially through the foam layer, and a drape sealable over the foam layer and a wound bed. The drape is couplable to a pump operable to create a negative pressure in the substantially-airtight volume. Each core is substantially removable from the foam layer to reveal a channel through the foam layer. Each core is defined by perforations that facilitate separation of the core from the foam layer.

20 Claims, 17 Drawing Sheets

(56) References Cited

U.S. PATENT DOCUMENTS

| | | |
|---|---|---|
| 2,682,873 A | 7/1954 | Evans et al. |
| 2,910,763 A | 11/1959 | Lauterbach |
| 2,969,057 A | 1/1961 | Simmons |
| 3,066,672 A | 12/1962 | Crosby, Jr. et al. |
| 3,367,332 A | 2/1968 | Groves |
| 3,520,300 A | 7/1970 | Flower, Jr. |
| 3,568,675 A | 3/1971 | Harvey |
| 3,648,692 A | 3/1972 | Wheeler |
| 3,682,180 A | 8/1972 | McFarlane |
| 3,826,254 A | 7/1974 | Mellor |
| 4,080,970 A | 3/1978 | Miller |
| 4,096,853 A | 6/1978 | Weigand |
| 4,139,004 A | 2/1979 | Gonzalez, Jr. |
| 4,165,748 A | 8/1979 | Johnson |
| 4,184,510 A | 1/1980 | Murry et al. |
| 4,233,969 A | 11/1980 | Lock et al. |
| 4,245,630 A | 1/1981 | Lloyd et al. |
| 4,256,109 A | 3/1981 | Nichols |
| 4,261,363 A | 4/1981 | Russo |
| 4,275,721 A | 6/1981 | Olson |
| 4,284,079 A | 8/1981 | Adair |
| 4,297,995 A | 11/1981 | Golub |
| 4,333,468 A | 6/1982 | Geist |
| 4,373,519 A | 2/1983 | Errede et al. |
| 4,382,441 A | 5/1983 | Svedman |
| 4,392,853 A | 7/1983 | Muto |
| 4,392,858 A | 7/1983 | George et al. |
| 4,419,097 A | 12/1983 | Rowland |
| 4,465,485 A | 8/1984 | Kashmer et al. |
| 4,475,909 A | 10/1984 | Eisenberg |
| 4,480,638 A | 11/1984 | Schmid |
| 4,525,166 A | 6/1985 | Leclerc |
| 4,525,374 A | 6/1985 | Vaillancourt |
| 4,540,412 A | 9/1985 | Van Overloop |
| 4,543,100 A | 9/1985 | Brodsky |
| 4,548,202 A | 10/1985 | Duncan |
| 4,551,139 A | 11/1985 | Plaas et al. |
| 4,569,348 A | 2/1986 | Hasslinger |
| 4,605,399 A | 8/1986 | Weston et al. |
| 4,608,041 A | 8/1986 | Nielsen |
| 4,640,688 A | 2/1987 | Hauser |
| 4,655,754 A | 4/1987 | Richmond et al. |
| 4,664,662 A | 5/1987 | Webster |
| 4,710,165 A | 12/1987 | McNeil et al. |
| 4,733,659 A | 3/1988 | Edenbaum et al. |
| 4,743,232 A | 5/1988 | Kruger |
| 4,758,220 A | 7/1988 | Sundblom et al. |
| 4,787,888 A | 11/1988 | Fox |
| 4,826,494 A | 5/1989 | Richmond et al. |
| 4,838,883 A | 6/1989 | Matsuura |
| 4,840,187 A | 6/1989 | Brazier |
| 4,863,449 A | 9/1989 | Therriault et al. |
| 4,872,450 A | 10/1989 | Austad |
| 4,878,901 A | 11/1989 | Sachse |
| 4,897,081 A | 1/1990 | Poirier et al. |
| 4,906,233 A | 3/1990 | Moriuchi et al. |
| 4,906,240 A | 3/1990 | Reed et al. |
| 4,919,654 A | 4/1990 | Kalt |
| 4,941,882 A | 7/1990 | Ward et al. |
| 4,953,565 A | 9/1990 | Tachibana et al. |
| 4,969,880 A | 11/1990 | Zamierowski |
| 4,985,019 A | 1/1991 | Michelson |
| 5,037,397 A | 8/1991 | Kalt et al. |
| 5,086,170 A | 2/1992 | Luheshi et al. |
| 5,092,858 A | 3/1992 | Benson et al. |
| 5,100,396 A | 3/1992 | Zamierowski |
| 5,134,994 A | 8/1992 | Say |
| 5,149,331 A | 9/1992 | Ferdman et al. |
| 5,167,613 A | 12/1992 | Karami et al. |
| 5,176,663 A | 1/1993 | Svedman et al. |
| 5,215,522 A | 6/1993 | Page et al. |
| 5,232,453 A | 8/1993 | Plass et al. |
| 5,261,893 A | 11/1993 | Zamierowski |
| 5,278,100 A | 1/1994 | Doan et al. |
| 5,279,550 A | 1/1994 | Habib et al. |
| 5,298,015 A | 3/1994 | Komatsuzaki et al. |
| 5,342,376 A | 8/1994 | Ruff |
| 5,344,415 A | 9/1994 | DeBusk et al. |
| 5,358,494 A | 10/1994 | Svedman |
| 5,437,622 A | 8/1995 | Carion |
| 5,437,651 A | 8/1995 | Todd et al. |
| 5,527,293 A | 6/1996 | Zamierowski |
| 5,549,584 A | 8/1996 | Gross |
| 5,556,375 A | 9/1996 | Ewall |
| 5,607,388 A | 3/1997 | Ewall |
| 5,636,643 A | 6/1997 | Argenta et al. |
| 5,645,081 A | 7/1997 | Argenta et al. |
| 6,071,267 A | 6/2000 | Zamierowski |
| 6,135,116 A | 10/2000 | Vogel et al. |
| 6,241,747 B1 | 6/2001 | Ruff |
| 6,287,316 B1 | 9/2001 | Agarwal et al. |
| 6,345,623 B1 | 2/2002 | Heaton et al. |
| 6,488,643 B1 | 12/2002 | Tumey et al. |
| 6,493,568 B1 | 12/2002 | Bell et al. |
| 6,553,998 B2 | 4/2003 | Heaton et al. |
| 6,814,079 B2 | 11/2004 | Heaton et al. |
| 2002/0077661 A1 | 6/2002 | Saadat |
| 2002/0115951 A1 | 8/2002 | Norstrem et al. |
| 2002/0120185 A1 | 8/2002 | Johnson |
| 2002/0143286 A1 | 10/2002 | Tumey |
| 2012/0116334 A1* | 5/2012 | Albert .................. A61F 13/02 604/319 |
| 2016/0120706 A1 | 5/2016 | Collinson et al. |
| 2017/0007751 A1* | 1/2017 | Hartwell ............ A61F 13/0206 |
| 2017/0143552 A1* | 5/2017 | Hartwell ............ A61F 13/0233 |

FOREIGN PATENT DOCUMENTS

| | | |
|---|---|---|
| AU | 755496 B2 | 12/2002 |
| CA | 2005436 A1 | 6/1990 |
| DE | 26 40 413 A1 | 3/1978 |
| DE | 43 06 478 A1 | 9/1994 |
| DE | 29 504 378 U1 | 9/1995 |
| EP | 0100148 A1 | 2/1984 |
| EP | 0117632 A2 | 9/1984 |
| EP | 0161865 A2 | 11/1985 |
| EP | 0358302 A2 | 3/1990 |
| EP | 1018967 A1 | 7/2000 |
| GB | 692578 A | 6/1953 |
| GB | 2 195 255 A | 4/1988 |
| GB | 2 197 789 A | 6/1988 |
| GB | 2 220 357 A | 1/1990 |
| GB | 2 235 877 A | 3/1991 |
| GB | 2 329 127 A | 3/1999 |
| GB | 2 333 965 A | 8/1999 |
| JP | 4129536 B2 | 8/2008 |
| SG | 71559 | 4/2002 |
| WO | 80/02182 A1 | 10/1980 |
| WO | 87/04626 A1 | 8/1987 |
| WO | 90/010424 A1 | 9/1990 |
| WO | 93/009727 A1 | 5/1993 |
| WO | 94/020041 A1 | 9/1994 |
| WO | 96/05873 A1 | 2/1996 |
| WO | 97/18007 A1 | 5/1997 |
| WO | 99/13793 A1 | 3/1999 |
| WO | WO-2014/020443 A2 | 2/2014 |
| WO | WO-2015/110410 A1 | 7/2015 |
| WO | WO-2015110410 A1 * | 7/2015 ......... A61F 13/0216 |
| WO | WO-2015/193257 A1 | 12/2015 |
| WO | WO-2015193257 A1 * | 12/2015 ....... A61F 13/00008 |

OTHER PUBLICATIONS

International Search Report and Written Opinion in International Application No. PCT/US2019/042009, dated Oct. 7, 2019.

Louis C. Argenta, MD and Michael J. Morykwas, PHD; Vacuum-Assisted Closure: A New Method for Wound Control and Treatment: Clinical Experience; Annals of Plastic Surgery; vol. 38, No. 6, Jun. 1997; pp. 563-576.

Susan Mendez-Eatmen, RN; "When wounds Won't Heal" RN Jan. 1998, vol. 61 (1); Medical Economics Company, Inc., Montvale, NJ, USA; pp. 20-24.

(56) References Cited

OTHER PUBLICATIONS

James H. Blackburn II, MD et al.: Negative-Pressure Dressings as a Bolster for Skin Grafts; Annals of Plastic Surgery, vol. 40, No. 5, May 1998, pp. 453-457; Lippincott Williams & Wilkins, Inc., Philidelphia, PA, USA.
John Masters; "Reliable, Inexpensive and Simple Suction Dressings"; Letter to the Editor, British Journal of Plastic Surgery, 1998, vol. 51 (3), p. 267; Elsevier Science/The British Association of Plastic Surgeons, UK.
S.E. Greer, et al. "The Use of Subatmospheric Pressure Dressing Therapy to Close Lymphocutaneous Fistulas of the Groin" British Journal of Plastic Surgery (2000), 53, pp. 484-487.
George V. Letsou, MD., et al; "Stimulation of Adenylate Cyclase Activity in Cultured Endothelial Cells Subjected to Cyclic Stretch"; Journal of Cardiovascular Surgery, 31, 1990, pp. 634-639.
Orringer, Jay, et al; "Management of Wounds in Patients with Complex Enterocutaneous Fistulas"; Surgery, Gynecology & Obstetrics, Jul. 1987, vol. 165, pp. 79-80.
International Search Report for PCT International Application PCT/GB95/01983; dated Nov. 23, 1995.
PCT International Search Report for PCT International Application PCT/GB98/02713; dated Jan. 8, 1999.
PCT Written Opinion; PCT International Application PCT/GB98/02713; dated Jun. 8, 1999.
PCT International Examination and Search Report, PCT International Application PCT/GB96/02802; dated Jan. 15, 1998 & Apr. 29, 1997.
PCT Written Opinion, PCT International Application PCT/GB96/02802; dated Sep. 3, 1997.
Dattilo, Philip P., Jr., et al; "Medical Textiles: Application of an Absorbable Barbed Bi-directional Surgical Suture"; Journal of Textile and Apparel, Technology and Management, vol. 2, Issue 2, Spring 2002, pp. 1-5.
Kostyuchenok, B.M., et al; "Vacuum Treatment in the Surgical Management of Purulent Wounds"; Vestnik Khirurgi, Sep. 1986, pp. 18-21 and 6 page English translation thereof.
Davydov, Yu. A., et al; "Vacuum Therapy in the Treatment of Purulent Lactation Mastitis"; Vestnik Khirurgi, May 14, 1986, pp. 66-70, and 9 page English translation thereof.
Yusupov. Yu.N., et al; "Active Wound Drainage", Vestnki Khirurgi, vol. 138, Issue 4, 1987, and 7 page English translation thereof.
Davydov, Yu.A., et al; "Bacteriological and Cytological Assessment of Vacuum Therapy for Purulent Wounds"; Vestnik Khirugi, Oct. 1988, pp. 48-52, and 8 page English translation thereof.
Davydov, Yu.A., et al; "Concepts for the Clinical-Biological Management of the Wound Process in the Treatment of Purulent Wounds by Means of Vacuum Therapy"; Vestnik Khirurgi, Jul. 7, 1980, pp. 132-136, and 8 page English translation thereof.
Chariker, Mark E., M.D., et al; "Effective Management of incisional and cutaneous fistulae with closed suction wound drainage"; Contemporary Surgery, vol. 34, Jun. 1989, pp. 59-63.
Egnell Minor, Instruction Book, First Edition, 300 7502, Feb. 1975, pp. 24.
Egnell Minor: Addition to the Users Manual Concerning Overflow Protection—Concerns all Egnell Pumps, Feb. 3, 1983, pp. 2.
Svedman, P.: "Irrigation Treatment of Leg Ulcers", The Lancet, Sep. 3, 1983, pp. 532-534.
Chinn, Steven D. et al.: "Closed Wound Suction Drainage", The Journal of Foot Surgery, vol. 24, No. 1, 1985, pp. 76-81.

Arnljots, Björn et al.: "Irrigation Treatment in Split-Thickness Skin Grafting of Intractable Leg Ulcers", Scand J. Plast Reconstr. Surg., No. 19, 1985, pp. 211-213.
Svedman, P.: "A Dressing Allowing Continuous Treatment of a Biosurface", IRCS Medical Science: Biomedical Technology, Clinical Medicine, Surgery and Transplantation, vol. 7, 1979, p. 221.
Svedman, P. et al.: "A Dressing System Providing Fluid Supply and Suction Drainage Used for Continuous of Intermittent Irrigation", Annals of Plastic Surgery, vol. 17, No. 2, Aug. 1986, pp. 125-133.
N.A. Bagautdinov, "Variant of External Vacuum Aspiration in the Treatment of Purulent Diseases of Soft Tissues," Current Problems in Modern Clinical Surgery: Interdepartmental Collection, edited by V. Ye Volkov et al. (Chuvashia State University, Cheboksary, U.S.S.R. 1986); pp. 94-96 (copy and certified translation).
K.F. Jeter, T.E. Tintle, and M. Chariker, "Managing Draining Wounds and Fistulae: New and Established Methods," Chronic Wound Care, edited by D. Krasner (Health Management Publications, Inc., King of Prussia, PA 1990), pp. 240-246.
G. Živadinovi?, V. ?uki?, Ž. Maksimovi?, ?. Radak, and p. Peška, "Vacuum Therapy in the Treatment of Peripheral Blood Vessels," Timok Medical Journal 11 (1986), pp. 161-164 (copy and certified translation).
F.E. Johnson, "An Improved Technique for Skin Graft Placement Using a Suction Drain," Surgery, Gynecology, and Obstetrics 159 (1984), pp. 584-585.
A.A. Safronov, Dissertation Abstract, Vacuum Therapy of Trophic Ulcers of the Lower Leg with Simultaneous Autoplasty of the Skin (Central Scientific Research Institute of Traumatology and Orthopedics, Moscow, U.S.S.R. 1967) (copy and certified translation).
M. Schein, R. Saadia, J.R. Jamieson, and G.A.G. Decker, "The 'Sandwich Technique' in the Management of the Open Abdomen," British Journal of Surgery 73 (1986), pp. 369-370.
D.E. Tribble, An Improved Sump Drain-Irrigation Device of Simple Construction, Archives of Surgery 105 (1972) pp. 511-513.
M.J. Morykwas, L.C. Argenta, E.I. Shelton-Brown, and W. McGuirt, "Vacuum-Assisted Closure: A New Method for Wound Control and Treatment: Animal Studies and Basic Foundation," Annals of Plastic Surgery 38 (1997), pp. 553-562 (Morykwas I).
C.E. Tennants, "The Use of Hypermia in the Postoperative Treatment of Lesions of the Extremities and Thorax," Journal of the American Medical Association 64 (1915), pp. 1548-1549.
Selections from W. Meyer and V. Schmieden, Bier's Hyperemic Treatment in Surgery, Medicine, and the Specialties: A Manual of Its Practical Application, (W.B. Saunders Co., Philadelphia, PA 1909), pp. 17-25, 44-64, 90-96, 167-170, and 210-211.
V.A. Solovev et al., Guidelines, The Method of Treatment of Immature External Fistulas in the Upper Gastrointestinal Tract, editor-in-chief Prov. V.I. Parahonyak (S.M. Kirov Gorky State Medical Institute, Gorky, U.S.S.R. 1987) ("Solovev Guidelines").
V.A. Kuznetsov & N.a. Bagautdinov, "Vacuum and Vacuum-Sorption Treatment of Open Septic Wounds," in II All-Union Conference on Wounds and Wound Infections: Presentation Abstracts, edited by B.M. Kostyuchenok et al. (Moscow, U.S.S.R. Oct. 28-29, 1986) pp. 91-92 ("Bagautdinov II").
V.A. Solovev, Dissertation Abstract, Treatment and Prevention of Suture Failures after Gastric Resection (S.M. Kirov Gorky State Medical Institute, Gorky, U.S.S.R. 1988) ("Solovev Abstract").
V.A.C. ® Therapy Clinical Guidelines: A Reference Source for Clinicians; Jul. 2007.

* cited by examiner

WOUND VIEW DRESSING AND CUSTOMIZATION KIT

CROSS-REFERENCE TO RELATED APPLICATIONS

This application claims the benefit of priority to U.S. Provisional Application No. 62/699,888, filed on Jul. 18, 2018, which is incorporated herein by reference in its entirety.

BACKGROUND

The present disclosure relates generally to wound therapy systems and devices, and more particularly to a dressing kit for use with negative pressure wound therapy.

Negative pressure wound therapy (NPWT) is a type of wound therapy that involves applying negative pressure (relative to atmospheric pressure) to a wound bed to promote wound healing. NPWT systems often include a dressing that covers the wound bed. Once applied to the wound bed, the dressing typically remains in place for several days before the dressing is removed. A patient or caregiver may desire to inspect the wound bed during this time to monitor the progress of healing and make adjustments to treatment as needed for various regions of the wound bed.

Various dressing materials are known to provide various therapeutic benefits to the wound when used in NPWT. Meanwhile, different therapeutic benefits may be suited for different portions of a wound bed. For example, one portion of the wound bed may require a dressing with high fluid absorption, while another portion may benefit from debridement by a relatively rough dressing material. A caregiver may therefore desire to use various dressing materials to treat a single wound bed. It would be beneficial to provide an NPWT dressing that provides in-situ wound viewing capability and/or that permits customization with various other dressing materials to facilitate discrete, regional changes to the wound therapy provided with the dressing.

SUMMARY

One implementation of the present disclosure is dressing. The dressing includes a foam layer, a plurality of cores extending substantially through the foam layer, and a drape sealable over the foam layer and a wound bed. The drape is couplable to a pump operable to create a negative pressure in the substantially-airtight volume. Each core is substantially removable from the foam layer to reveal a channel through the foam layer. Each core is defined by perforations that facilitate separation of the core from the foam layer.

In some embodiments, each core is substantially removable from the foam layer by cutting a hole through the drape at a location of the core and extracting the core from the foam layer through the hole. In some embodiments, the dressing also includes a patch sealable over the hole to reseal the substantially-airtight volume. In some embodiments, a cutting template positioned between the drape and the selected core facilitates cutting the hole through the drape. In some embodiments, the wound bed is visible through the channel when the core is removed. In some embodiments, the channel is configured to receive a replacement core. The foam layer and the replacement core have one or more differing physical characteristics.

Another implementation of the present disclosure is a dressing kit. The dressing kit includes a foam layer with a plurality of removable cores extending therethrough. The dressing kit also includes a drape configured to seal the foam layer over a wound bed. The drape allows a hole to be created therethrough. The hole allows one of the plurality of removable cores to be removed from the foam layer to create a channel through the foam layer. The dressing kit also includes one or more patches. Each patch is sealable to the drape to close the hole in the drape.

In some embodiments, the dressing kit also includes a variety of replacement cores configured to be received by the channel. The variety of replacement cores are associated with a variety of therapeutic benefits. In some embodiments, the replacement cores include one or more of a high-density core, a low-density core, a debridement core, a cleansing core, a silver ion foam core, a hydrophobic core, a hydrophilic core, or a fluid collection core.

In some embodiments, the dressing kit also includes one or more cutting templates. Each cutting template is positionable between one of the plurality of removable cores and the drape to facilitate creation of the hole. In some embodiments, each cutting template has a shape that matches a cross-sectional shape of one or more of the plurality of removable cores.

In some embodiments, the dressing kit also includes a trackpad couplable to the drape. The trackpad is configured to provide fluid communication between the wound bed and a pump operable to create a negative pressure at the wound bed. In some embodiments, replacing one or more of the removable cores with one or more of the variety of replacement cores alters a compressibility profile of the foam dressing.

Another implementation of the present disclosure is a method for treating a wound. The method includes placing a foam layer on the wound. A plurality of cores extends through the foam layer. The method also includes sealing the foam layer over the wound with a drape, cutting a hole through the drape, removing a first core of the plurality of cores through the hole to create a channel through the foam layer to the wound, placing the first core or a replacement core in the channel, and sealing the hole with a patch.

In some embodiments, the replacement core has one or more material properties different than the first core. In some embodiments, the replacement core includes a high-density core, a low-density core, a debridement core, a cleansing core, a sliver foam core, a hydrophobic core, a hydrophilic core, or a fluid collection core.

In some embodiments, the method also includes targeting a therapy to a portion of the wound visible through the channel by selecting the replacement core from a kit of replacement cores having various therapeutic benefits and placing the replacement core in the channel proximate the portion. The replacement core is configured to provide the therapy.

In some embodiments, the method also includes cutting a plurality of additional holes through the drape, removing additional cores of the plurality of cores through the plurality of additional holes, replacing the additional cores with a plurality of replacement cores, and resealing the holes with a plurality of patches.

In some embodiments, the plurality of replacement cores has a variety of densities. The method also includes customizing a compressibility profile of the foam layer by arranging the plurality of replacement cores to provide the foam layer with a variable density.

DETAILED DESCRIPTION

Figure 1:
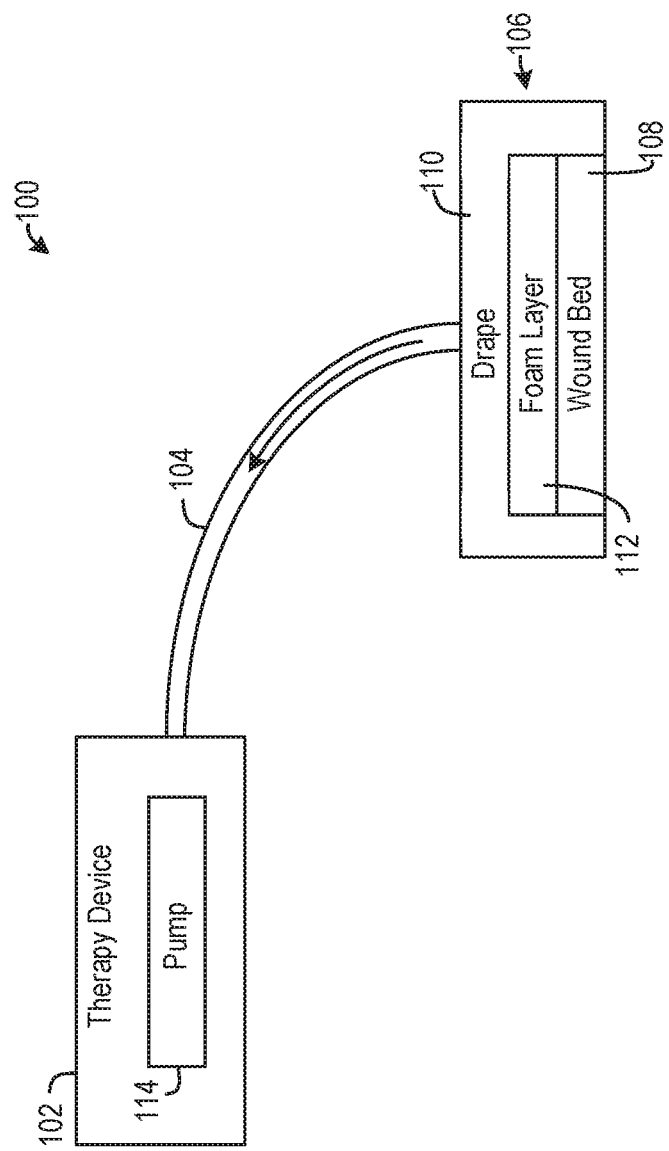
FIG. 1 is a block diagram of a negative pressure wound therapy (NPWT) system, according to an exemplary embodiment.

Referring now to FIG. 1, a negative pressure wound therapy (NPWT) system 100 is shown, according to an exemplary embodiment. The NPWT system 100 includes a therapy device 102 fluidly connected via a tube 104 to a dressing 106 substantially sealed over a wound bed 108. The wound bed 108 is a tissue wound on a patient, for example a trauma wound, a chronic wound, a third-degree burn, etc. The dressing 106 includes a foam layer 112 positioned at the wound bed 108 and a drape 110 that seals the foam layer 112 to the wound bed 108. As shown in FIG. 1, the foam layer 112 is sealed within a substantially air-tight volume between the drape 110 and the wound bed 108.

The therapy device 102 is configured to provide negative pressure wound therapy by reducing the pressure at wound bed 108. More particularly, therapy device 102 includes a pump 114 operable to draw a negative pressure (relative to atmospheric pressure) at wound bed 108 by removing wound exudate, air, and other fluids or debris from the foam layer 112 via tube 104. Wound exudate may include water and dissolved solutes such as blood, plasma proteins, white blood cells, platelets, and red blood cells. Removing fluid from the wound bed 108 helps to minimize fluid pooling in the wound bed 108 and prevent complications associated with maceration in order to promote wound healing. Negative pressure at the wound bed 108 may increase blood flow to the wound bed 108, reduce infection risks, and provide other benefits to the patient.

In use, the dressing 106 may preferably remain adhered to a patient for several days to minimize disruptions to the healing of the wound bed 108. During that time period, as described in detail below, the dressing 106 is configured to allow a caregiver to access the wound bed 108 and customize therapy for the wound bed 108 without removing the dressing 106. The dressing 106 thus allows a caregiver to continue to monitor the wound bed 108 and update treatment as needed without removing the dressing 106 or significantly disrupting the healing process.

Figure 2:
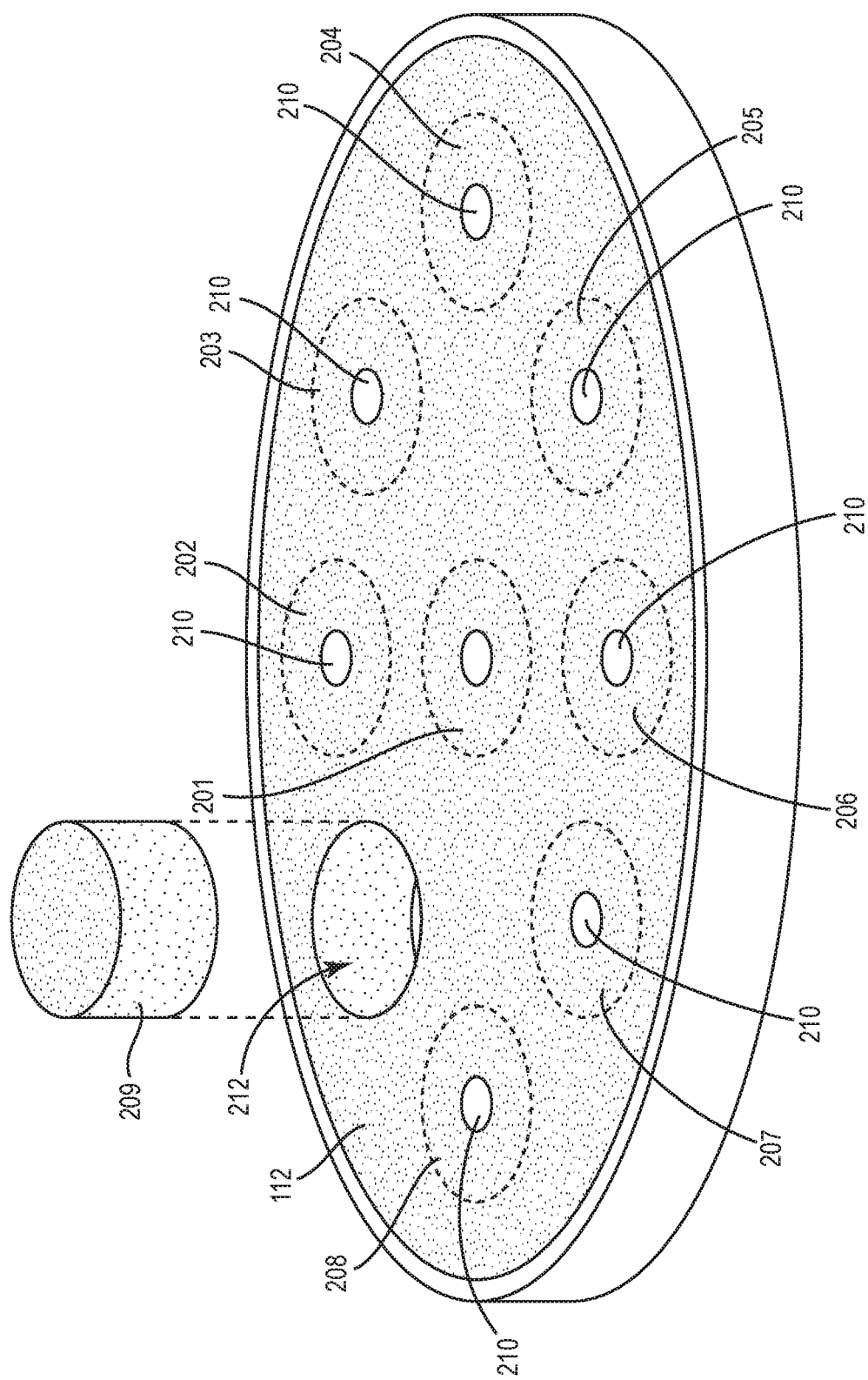
FIG. 2 is a top view of a foam layer for use with the NPWT system of FIG. 1, according to an exemplary embodiment.

Referring now to FIG. 2, a top view of the foam layer 112 is shown, according to an exemplary embodiment. The foam layer 112 may be manufactured from a polyurethane foam, for example V.A.C.® GranuFoam™ by Acelity. The foam layer 112 may have an open pore structure that facilitates the uniform distribution of negative pressure at the wound bed 108, and may have a hydrophobic property that facilitates removal of wound exudate from the dressing 106. The foam layer 112 may be flexible such that it forms to fit a wound bed 108 having an irregularly contoured shape.

The foam layer 112 includes a plurality of removable cores (e.g., modules, etc.), shown in the embodiment of FIG. 2 as first removable core 201, second removable core 202, third removable core 203, fourth removable core 204, fifth removable core 205, sixth removable core 206, seventh removable core 207, eighth removable core 208, and ninth removable core 209. Various other embodiments of foam layer 112 may include various numbers of removable cores (e.g., 1, 2, 3, 4, 5, 10, 20, etc.). The number of removable cores may be determined based on the size of the dressing 106 or wound bed 108. As shown in FIG. 2, the removable cores 201-209 are dispersed around the foam layer 112. The removable cores 201-209 are thereby arranged to align with a variety of portions of the wound bed 108. In various embodiments, the removable cores 201-209 are positioned in various arrangements (e.g., uniform, non-uniform, geometric patterns, random, etc.).

In the embodiments shown herein, each removable core 201-209 is substantially cylindrical. In various other embodiments, the removable cores 201-209 may be rectangular prisms, pyramidal sections, conical sections, frusto-conical sections, and/or some other form including an irregular or customizable form. The removable cores 201-209 extend through the foam layer 112 and may be coterminous with the foam layer 112 (i.e., each removable core 201-209 may have a height equal to a thickness of the foam layer 112). The removable cores 201-209 are each shown to include a dimple 210 that may facilitate identification, location, and manipulation of the removable cores 201-209. The removable cores 201-209 may be manufactured from the same material and have the same properties as the rest of the foam layer 112, or may have a different color, density, or other property to facilitate identification, location, and manipulation of the removable cores 201-209.

The removable cores 201-209 are each removable from the foam layer 112. Before removal, each removable core 201-209 may be attached to the foam layer 112 by several foam "bridges" separated by perforations. In other words, each removable core 201-209 may be defined by a ring of perforations that extends around the removable core 201-209. Each removable core 201-209 is thereby configured to be selectively removed from the foam layer 112 by tearing or cutting the foam bridges (i.e., tearing along the perforations) to separate the removable core 201-209 from the foam layer 112. The selected removable core 201-209 can then be freely extracted from the foam layer 112.

As shown in FIG. 2 for illustrative purposes, the ninth removable core 209 has been removed from the foam layer 112 to create a channel 212 (e.g., port, opening, window, passage, etc.) through the foam layer 112. Any one or more of the cores 201-209 may be removed as needed. The channel 212 has a substantially cylindrical form that matches the substantially cylindrical shape of the ninth removable core 209. The channel 212 allows a patient or caregiver to see through the foam layer 112 and to insert tools, fluid, medication, or other items for wound treatment through the foam layer 112 after treatment/inspection. The ninth removable core 209 may be replaced in the channel 212. As described in detail below, the channel 212 is also configured to receive a replacement core that may have one or more material properties (e.g., density, porosity, chemical composition, hydrophilia, texture) different than the ninth removable core 209, as may be desirable for treatment of the wound (e.g., as may be determined to be advantageous based upon inspection through channel 212).

Figure 3:
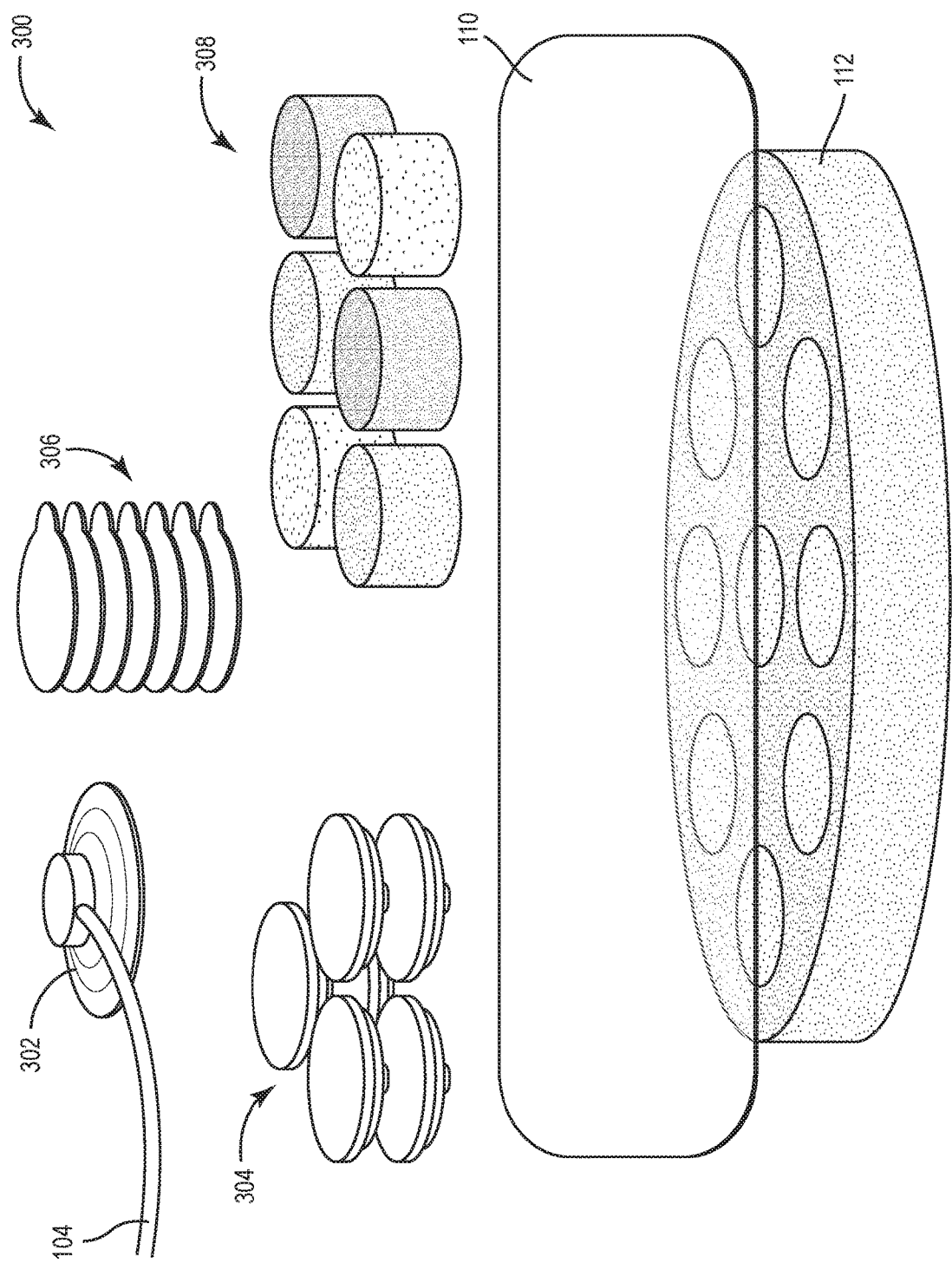
FIG. 3 is an illustration of a dressing kit for use the NPWT system of FIG. 1, according to an exemplary embodiment.

Referring now to FIG. 3, a dressing kit 300 for use with the NPWT system 100 is shown, according to an exemplary embodiment. The dressing kit 300 includes a drape 110, a foam layer 112, a trackpad 302 coupled to a tube 104, a plurality of cutting templates 304, a plurality of patches 306, and a plurality of replacement cores 308. As illustrated in FIGS. 4-16 and described in detail below, the dressing kit 300 may be used to apply a dressing 106 to a wound bed 108 and, without removing the dressing 106, access the wound bed 108 for inspection/treatment and to customize a therapy regime for the wound bed 108.

Still referring to FIG. 3, the drape 110 of the dressing kit 300 is a substantially air-impermeable sheet. The drape 110 may be transparent or translucent. The drape 110 may include an adhesive configured to allow the drape 110 to be coupled to a patient (i.e., a patient's skin in the periwound around a wound bed 108) and, in some embodiments, to the foam layer 112. The drape 110 is configured to allow a hole to be made therethrough with a sharp tool (e.g., knife, scissors, scalpel, etc.).

The foam layer 112 of the dressing kit 300 is described above with reference to FIG. 2 and elsewhere herein. In some embodiments, the dressing kit 300 includes various foam layers 112 of various shapes and sizes to accommodate various wounds.

The trackpad 302 is configured to couple the drape 110 to the tube 104 to place the dressing 106 in fluid communication with the therapy device 102. The trackpad 302 includes an adhesive to couple the trackpad 302 to the drape 110. The tube 104 is coupled to the trackpad 302 such that fluid can flow through the trackpad 302 and into the tube 104. When the dressing 106 is applied to a wound bed 108 as described herein, the trackpad 302 allows air to flow from the foam layer 112 to the therapy device 102 such that the pump 114 can create a negative pressure at the wound bed 108. The trackpad 302 may also include one or more sensors to facilitate NPWT.

The cutting templates 304 of the dressing kit 300 are configured to assist a user in cutting a hole through the drape 110 through which a removable core 201-209 can be removed and/or through which the tube 104 may be placed in fluid communication with the foam layer 112 by the trackpad 302. Various designs for the cutting templates 304 are possible, for example as shown and described in U.S. Provisional Patent Application No. 62/656,642 filed Apr. 12, 2018, incorporated by reference in its entirety herein, and U.S. Design Patent Application 29/643,866, filed Apr. 12, 2018 incorporated by reference in its entirety herein. The dressing kit 300 may include any suitable number of cutting templates 304 (e.g., one, three, five), for example an equal number of cutting templates 304 and removable cores 201-209.

The patches 306 of the dressing kit 300 are configured to reseal holes cut in the drape 110 using the cutting templates 304. The patches 306 are made of a substantially air-impermeable material and include an adhesive that allows the patches 306 to be sealed to the drape 110. The patches 306 may be shaped substantially the same as the cutting templates 304 but with a slightly larger area (i.e., an area greater than the area of a hole made using a cutting template 304). The patches 306 may include an adhesive or other coupling that allows the patches 306 to be selectively and repeatedly sealed to the drape 110, removed from the drape 110, and resealed to the drape 110. Each patch 306 may include an adhesive-free tab that facilitates removal of the patch 306 from the drape 110. The dressing kit 300 may include any number of patches 306 (e.g., 3, 5, 10), for example the same number of patches 306 as removable cores 201-209.

The replacement cores 308 of the drape 110 are configured to take the place of the removable cores 201-209 in the foam layer 112. Accordingly, the replacement cores 308 are sized and shaped substantially the same as the removable cores 201-209. The replacement cores 308 may differ from the removable cores 201-209 in chemical composition, density, color, absorptivity, and/or some other physical characteristics. In some embodiments, a replacement core 308 may include layers of varied materials or densities.

The dressing kit 300 may include a variety of replacement cores 308 associated with one or more of a variety of therapeutic benefits. In various embodiments, the variety of replacement cores 308 includes, by way of non-limiting example, one or more of a high-density core, a low-density core, a debridement core, a cleansing core, a sliver ion foam core, a hydrophobic core, a hydrophilic core, and/or a fluid collection core. The variety of replacement cores 308 allows a replacement core 308 to be selected from the dressing kit 300 and inserted into the foam layer 112 to customize a treatment profile of the dressing 106.

Referring now to FIGS. 4-16, a sequence of illustrations visualizing a process for treating a wound with the dressing kit 300 is shown, according to an exemplary embodiment. Each of FIGS. 4-16 illustrates a step of such a process. It should be understood that the sequence illustrated in FIGS. 4-16 is merely exemplary and that many similar sequences are made possible by the dressing kit 300. Further, the steps in the sequence may be rearranged or omitted as may be appropriate for a particular treatment plan.

Figure 4:
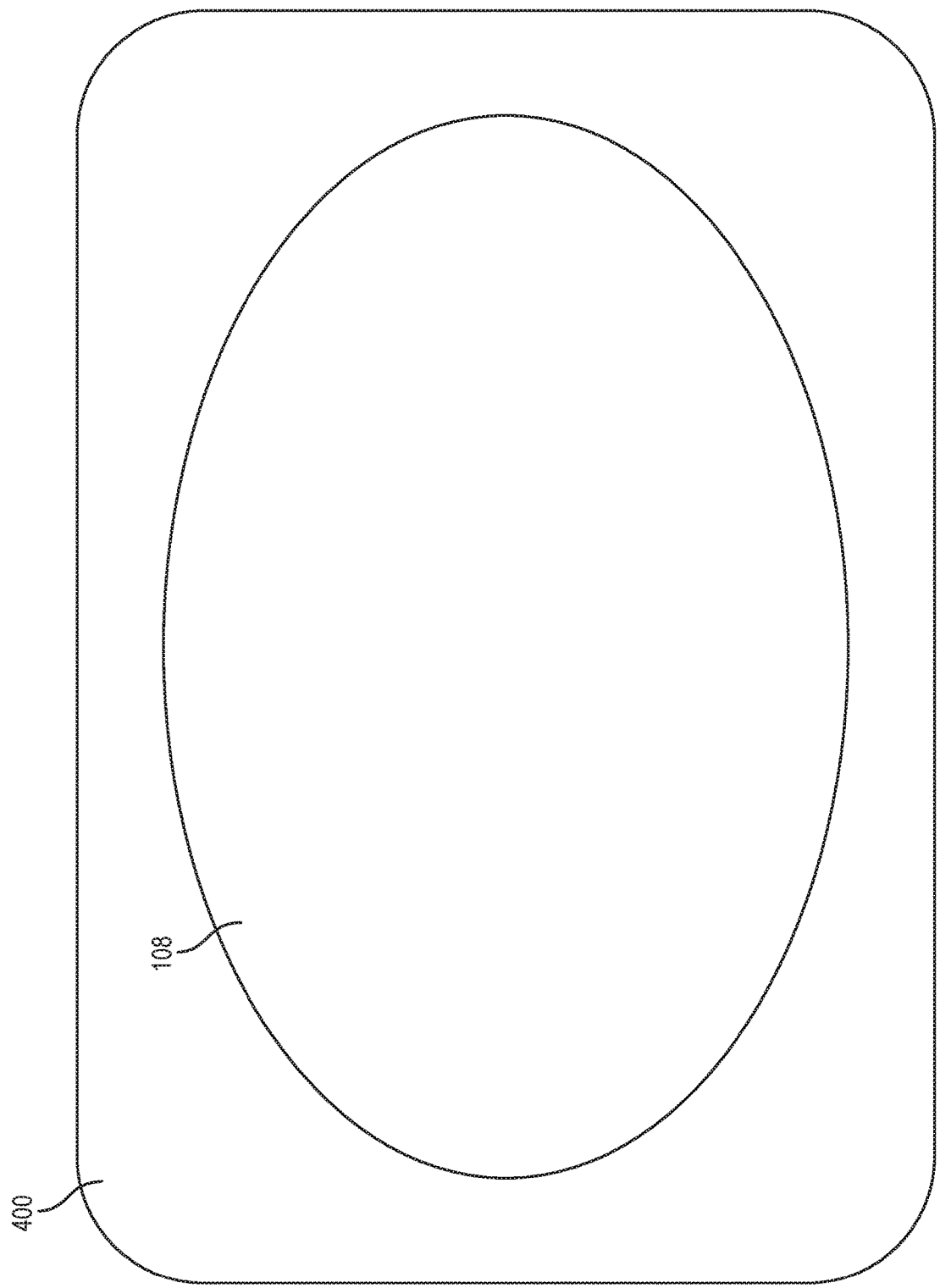
FIG. 4 is a schematic representation of a wound bed which may be treated using the dressing kit of FIG. 3, according to an exemplary embodiment.

Referring now to FIG. 4, the wound bed 108 is shown without the dressing 106. The wound bed 108 is surrounded by the periwound 400 (i.e., the unwounded area around the wound). The wound bed 108 and the periwound 400 may be prepared to receive the dressing 106, for example by cleaning the wound bed 108 and/or the periwound 400 and adding an antibiotic or other medication to the wound bed 108.

Figure 5:
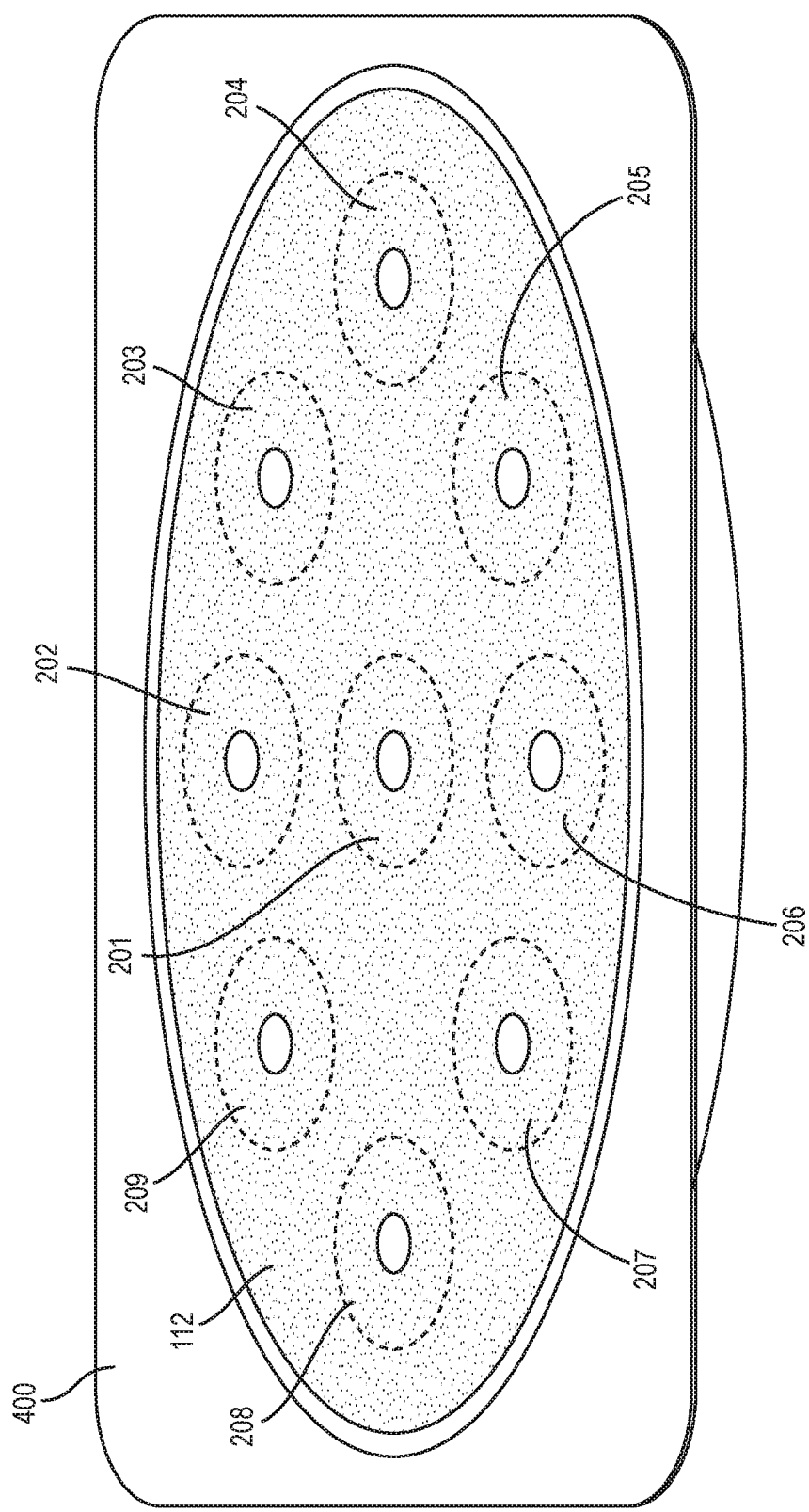
FIG. 5 is an illustration of a first step of providing NPWT to the wound bed of FIG. 4 with the dressing kit of FIG. 3, according to an exemplary embodiment.

Referring now to FIG. 5, the foam layer 112 is placed in the wound bed 108. The foam layer 112 may be shaped (e.g., cut) as needed to substantially match the shape of the wound bed 108. The foam layer 112 abuts the wound bed 108. The removable cores 201-209 are positioned over the wound bed 108. In some cases, one or more of the removable cores 201-209 are positioned over the periwound 400 or over the boundary between the wound bed 108 and the periwound 400 to facilitate monitoring and treatment of the periwound 400.

Figure 6:
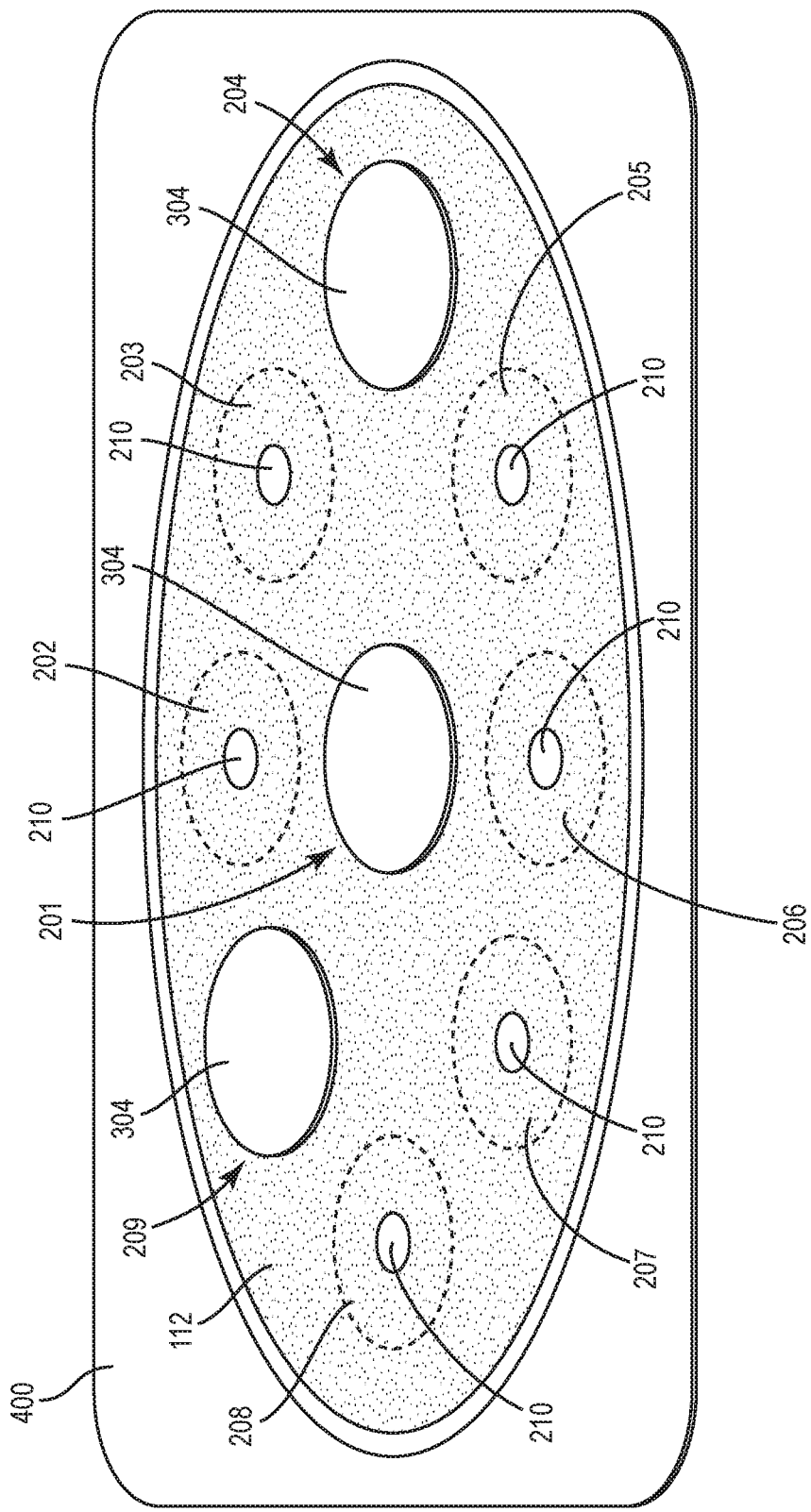
FIG. 6 is an illustration of a second step of providing NPWT to the wound bed of FIG. 4 with the dressing kit of FIG. 3, according to an exemplary embodiment.

Referring now to FIG. 6, several cutting templates 304 are placed on the foam layer 112. In the example shown, a cutting template 304 is placed at the first removable core 201, the fourth removable core 204, and the ninth removable core 209. In various other examples, cutting templates 304 may be placed on any or all of the removable cores 201-209 to suit a particular treatment plan. The dimples 210 on the removable cores 201-209 may engage a protrusion on the cutting templates 304 to help align the cutting templates 304 with the removable cores 201-209 and restrict the cutting templates 304 from sliding out of alignment with the removable cores 201-209.

Figure 7:
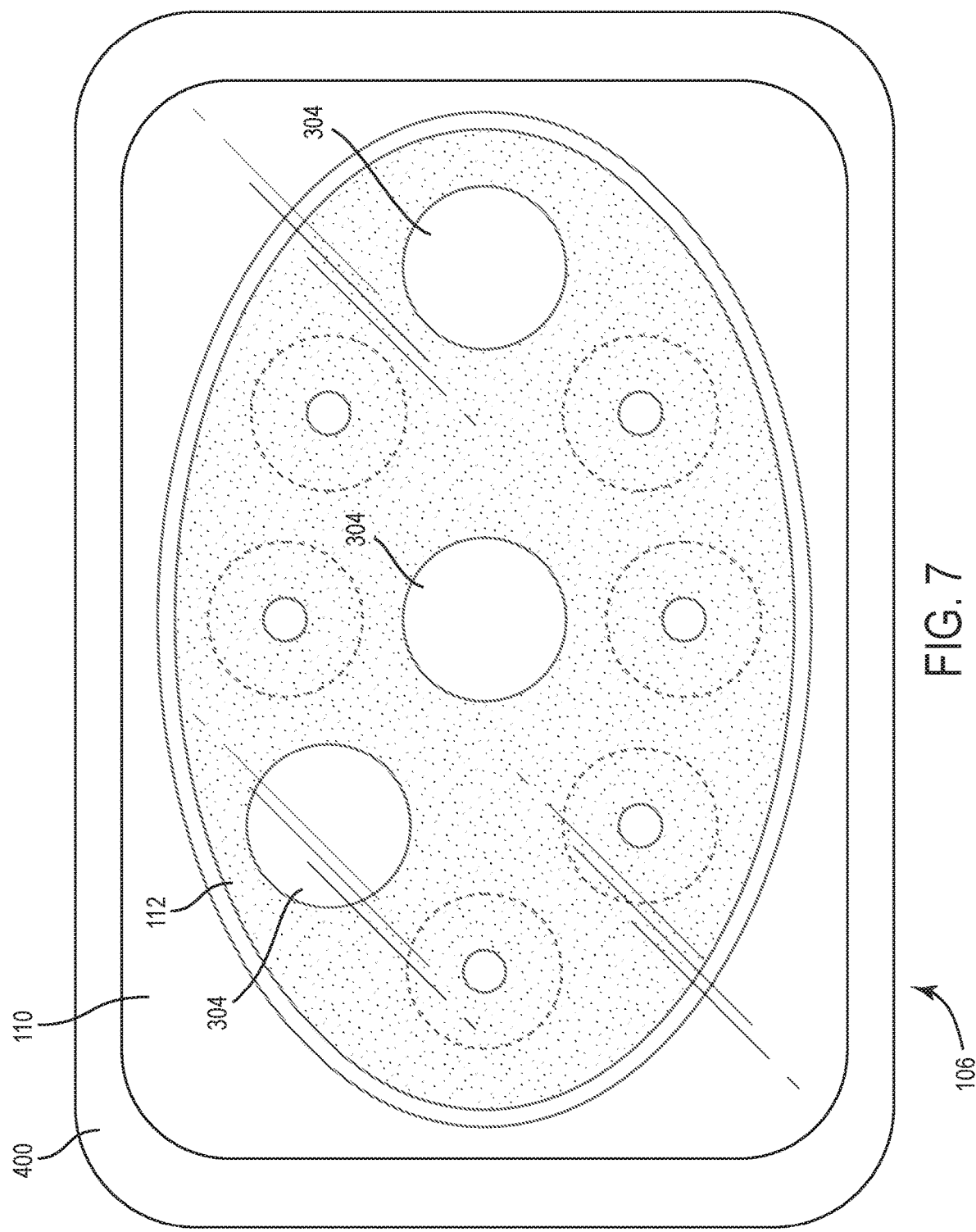
FIG. 7 is an illustration of a third step of providing NPWT to the wound bed of FIG. 4 with the dressing kit of FIG. 3, according to an exemplary embodiment.

Referring now to FIG. 7, the drape 110 is sealed over the foam layer 112 and the wound bed 108 and coupled to the periwound 400. For example, the drape 110 may include an adhesive that adheres the drape 110 to the periwound 400 (i.e., to the patient's skin) in an air-tight manner. The foam layer 112 is sealed in a substantially-airtight volume between the drape 110 and the wound bed 108. The cutting templates 304 abut the foam layer 112 and the drape 110. The drape 110 may be transparent or translucent such that the foam layer 112 and the cutting templates 304 are visible through the drape 110.

Figure 8:
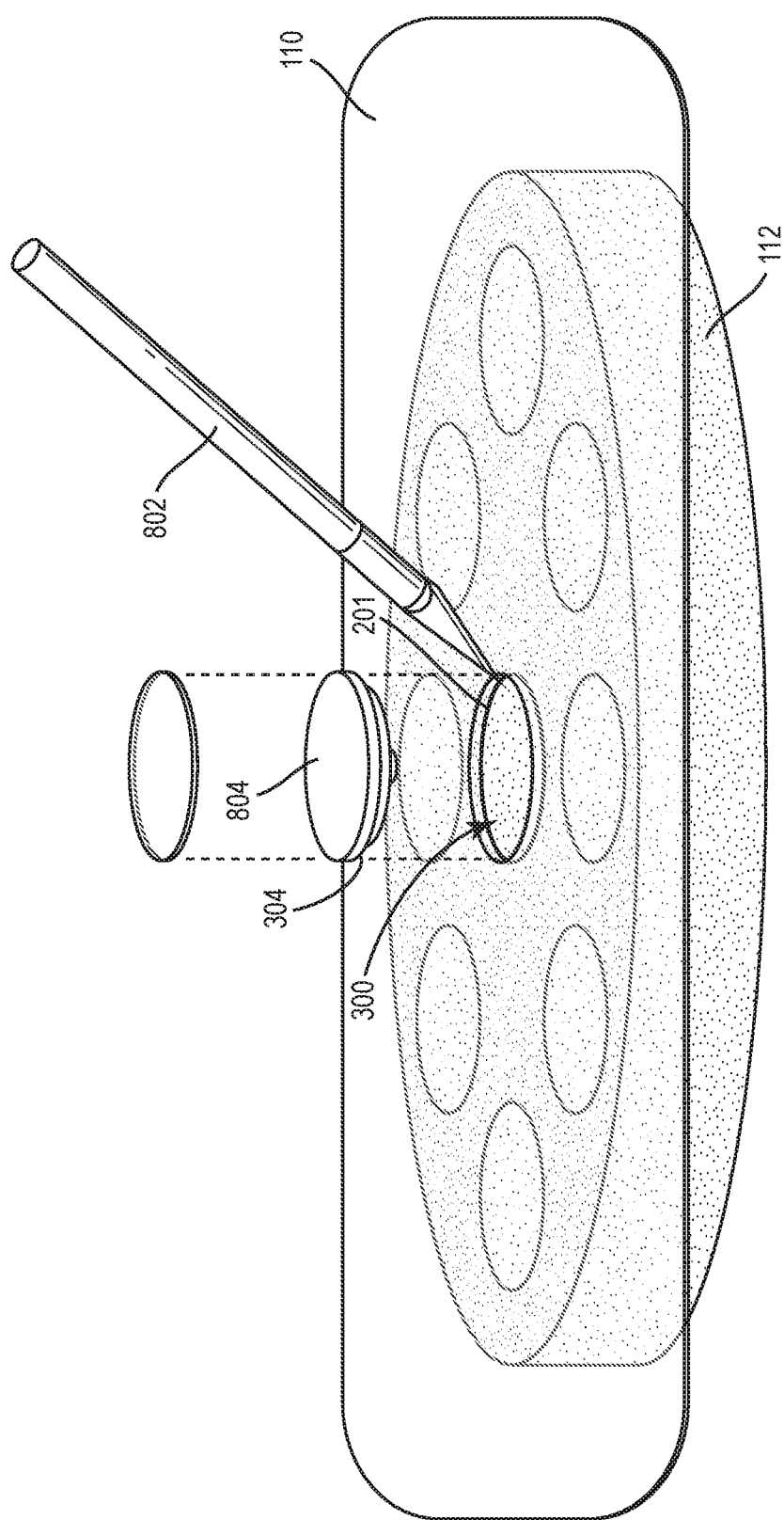
FIG. 8 is an illustration of a fourth step of providing NPWT to the wound bed of FIG. 4 with the dressing kit of FIG. 3, according to an exemplary embodiment.

Referring now to FIG. 8, the drape 110 is cut around a cutting template 304. In the example shown, a hole 800 is made in the drape 110 using a scalpel 802 guided by the cutting template 304. Other sharp tools (e.g., knife, scissors) may also be used. The hole 800 aligns with the first removable core 201. The cutting template 304 and a portion 804 of the drape 110 corresponding to the hole 800 may then be removed and discarded. According to some embodiments, the cutting template may be omitted.

Figure 9:
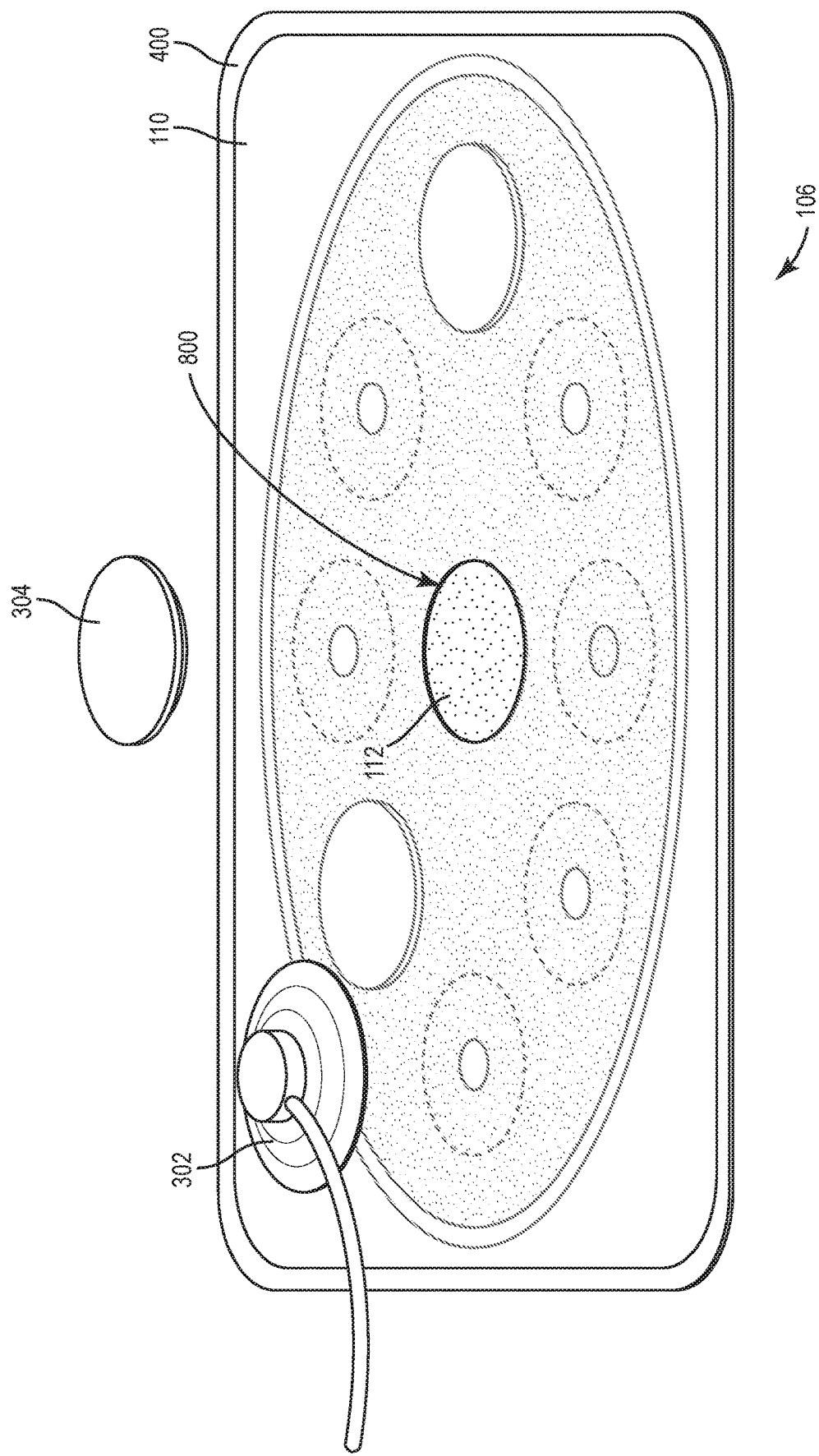
FIG. 9 is an illustration of a fifth step of providing NPWT to the wound bed of FIG. 4 with the dressing kit of FIG. 3, according to an exemplary embodiment.

Referring now to FIG. 9, the drape 110 is prepared to receive the trackpad 302. The cutting template 304 and a portion 804 of the drape 110 corresponding to the hole 800 has been removed. As shown in FIG. 9, the hole 800 extends through the drape 110 and allows fluid to flow therethrough, from the external environment to the foam layer 112 and vice versa.

Figure 10:
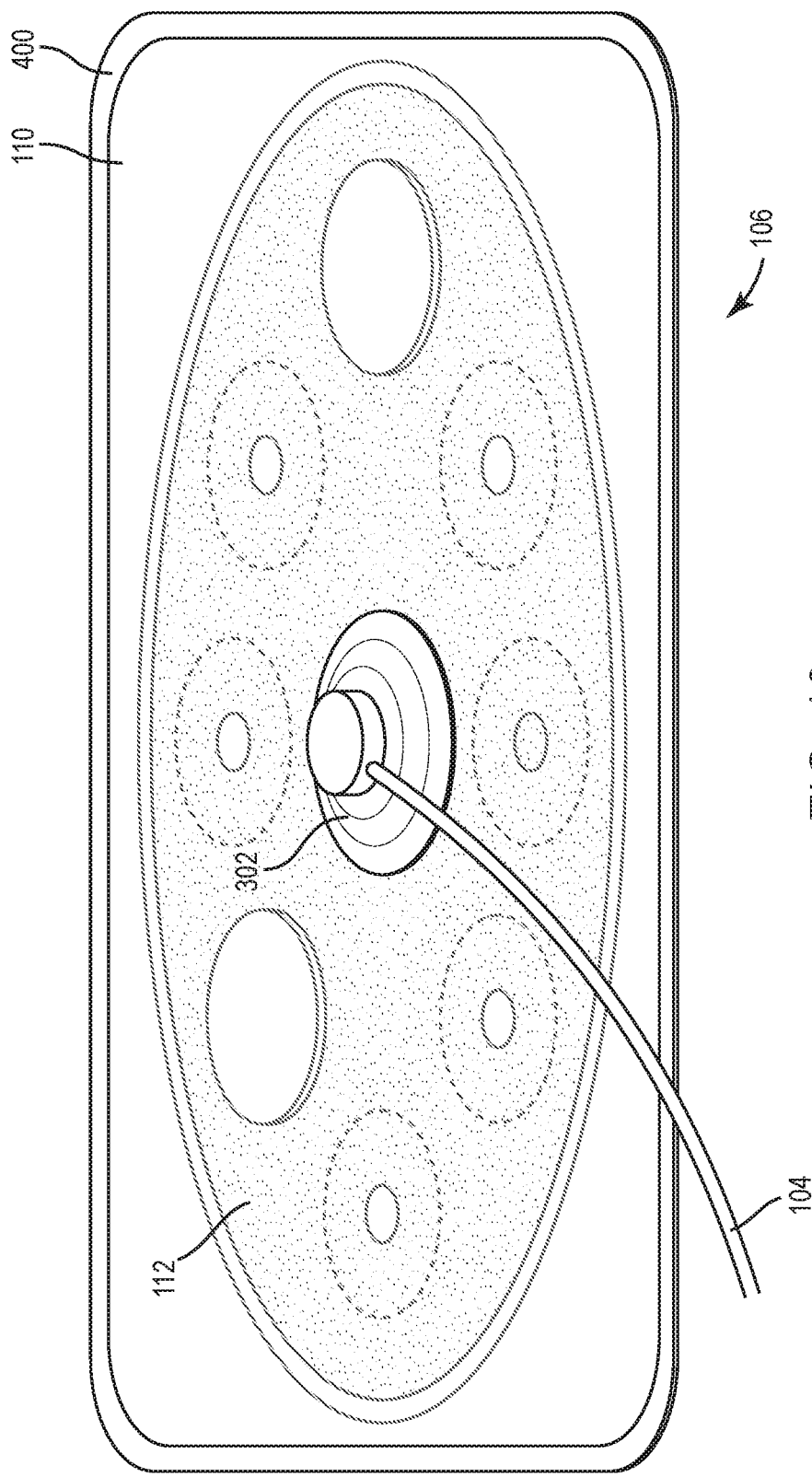
FIG. 10 is an illustration of a sixth step of providing NPWT to the wound bed of FIG. 4 with the dressing kit of FIG. 3, according to an exemplary embodiment.

Referring now to FIG. 10, the trackpad 302 is coupled to the drape 110 covering the hole 800. The tube 104 is fluidly communicable with the foam layer 112 via the trackpad 302 and the hole 800. The trackpad 302 is sealed to the drape 110 around the hole 800 such that fluid is substantially prevented from leaking between the trackpad 302 and the drape 110. The tube 104 may be coupled to the therapy device 102 and the pump 114, and NPWT may be initiated. That is, the pump 114 may create a negative pressure in the volume between the drape 110 and the wound bed 108 (i.e., in the foam layer 112) by pumping air and other fluid out of the volume via the tube 104. NPWT may then be continued for a desired duration of time.

Figure 11:
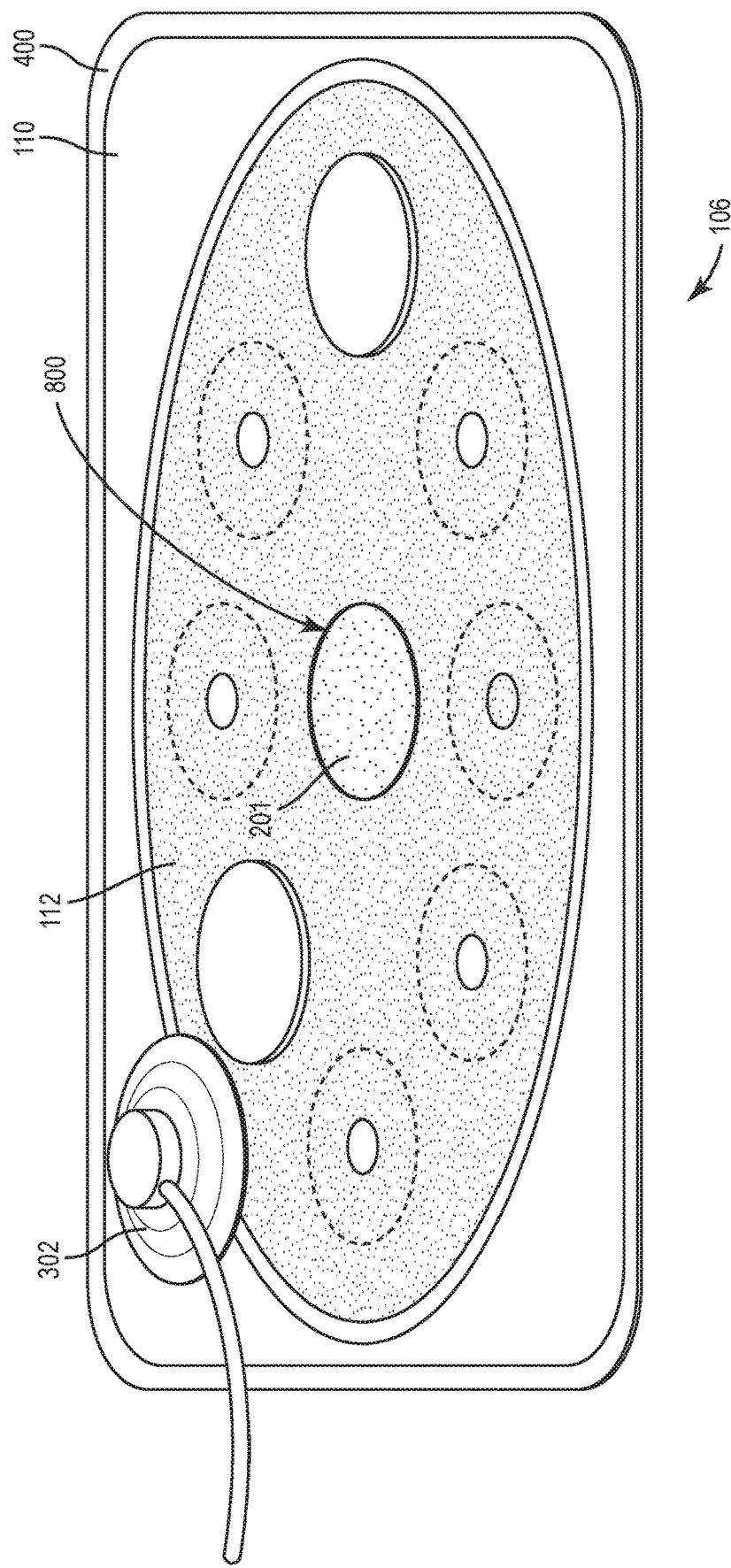
FIG. 11 is an illustration of a seventh step of providing NPWT to the wound bed of FIG. 4 with the dressing kit of FIG. 3, according to an exemplary embodiment.

Referring now to FIG. 11, negative pressure is released and the trackpad 302 is removed from the drape 110. Removing the trackpad 302 exposes the first removable core 201 through the hole 800. While in the configuration shown in FIG. 11, the first removable core 201 may be separated from the foam layer 112 by tearing or cutting along perforations that separate the first removable core 201 from the foam layer 112.

Figure 12:
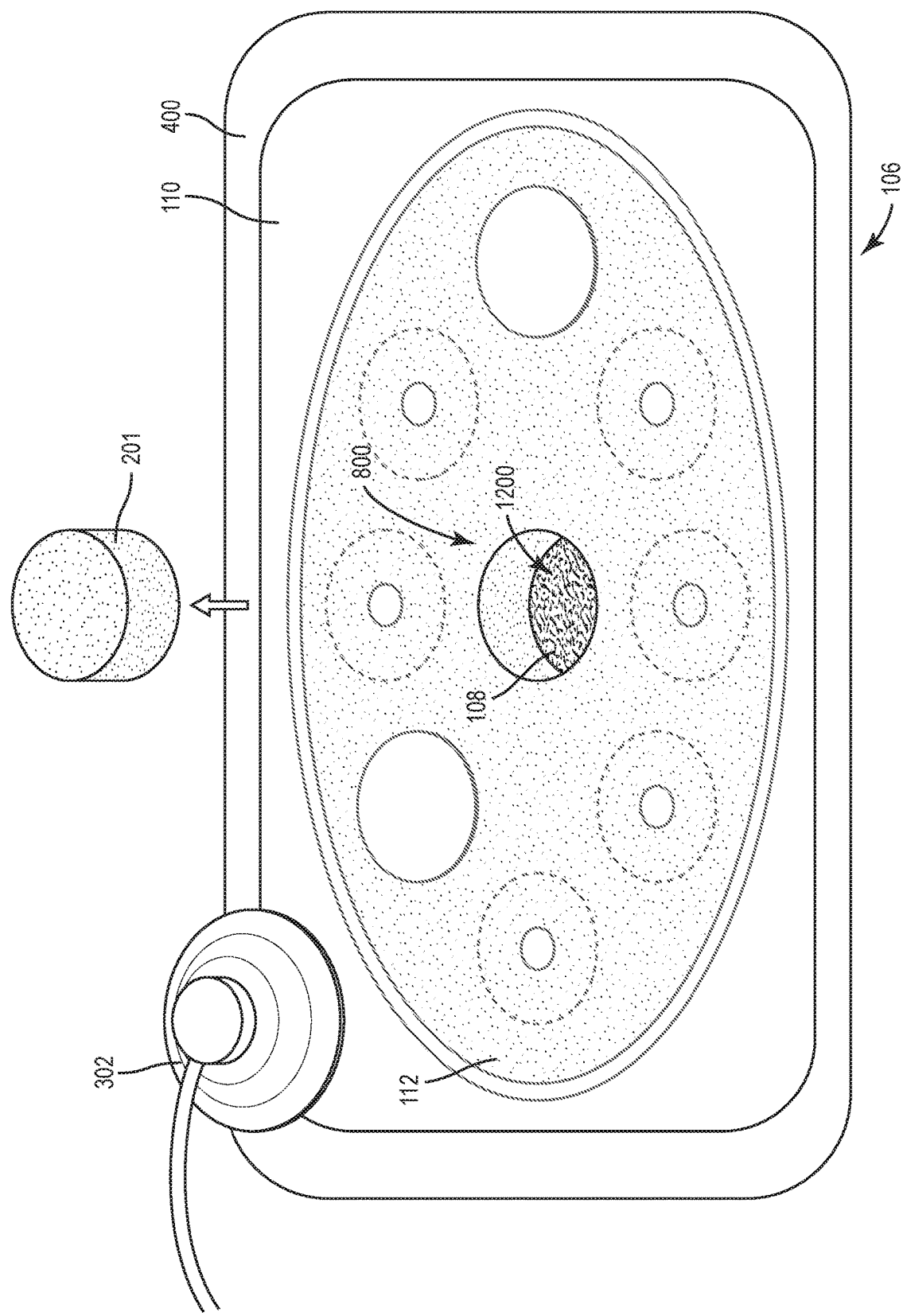
FIG. 12 is an illustration of an eighth step of providing NPWT to the wound bed of FIG. 4 with the dressing kit of FIG. 3, according to an exemplary embodiment.

Referring now to FIG. 12, the first removable core 201 is shown removed by way of example from the foam layer 112 via the hole 800. Removing the first removable core 201 from the foam layer 112 creates a channel 1200 extending through the drape 110 and the foam layer 112. The wound bed 108 is visible through the channel 1200, facilitating monitoring and diagnosis of the wound bed 108. The wound bed 108 may also be inspected, treated, contacted, altered, etc. via the channel 1200. Medication or other substance or object may be applied to the wound bed 108 via the channel 1200.

Figure 13:
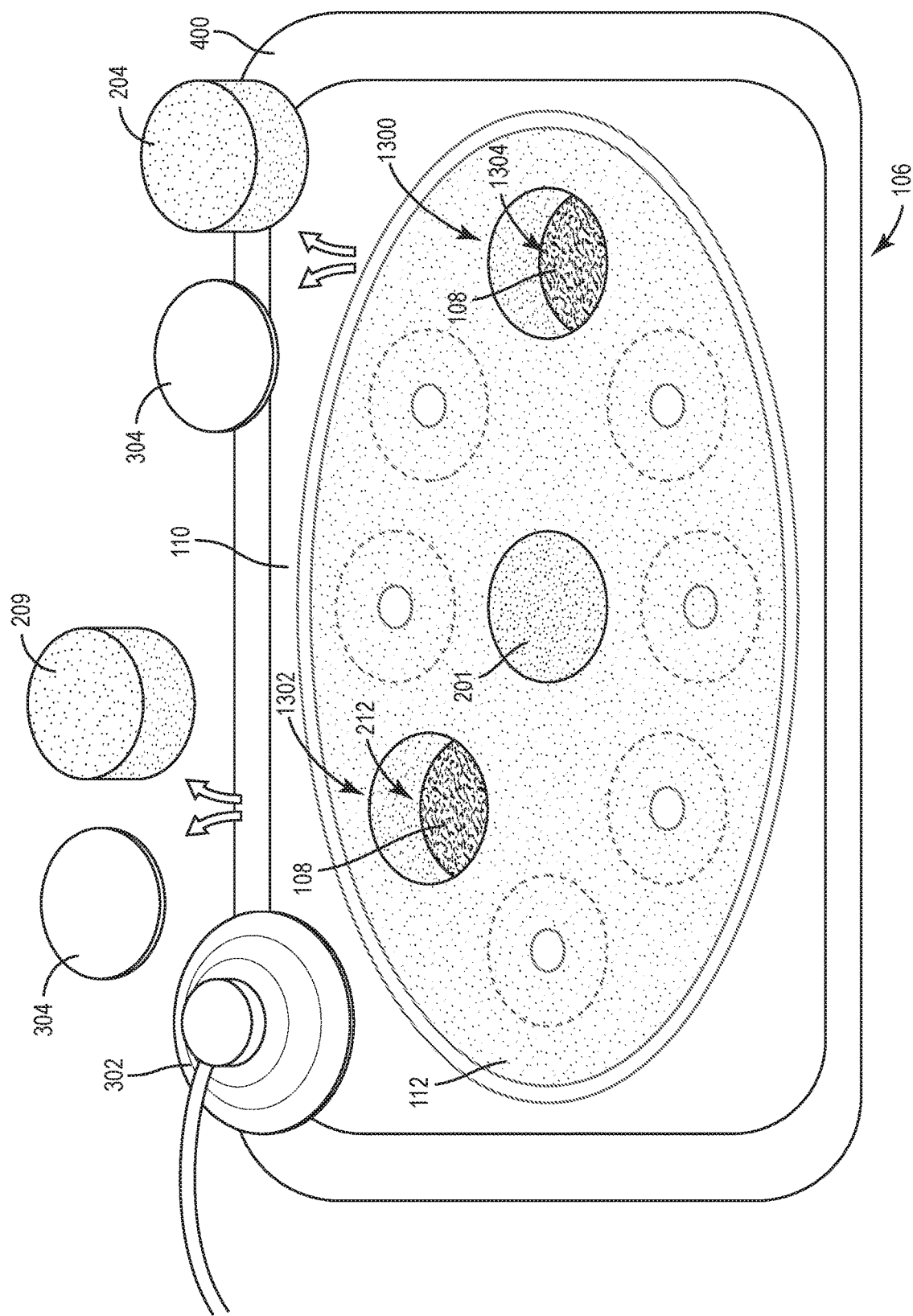
FIG. 13 is an illustration of a ninth step of providing NPWT to the wound bed of FIG. 4 with the dressing kit of FIG. 3, according to an exemplary embodiment.

Referring now to FIG. 13, the first removable core 201 is placed back in the channel 1200. In other examples, a replacement core 308 is placed in the channel 1200 to replace the first removable core 201. By way of illustrative example, a hole 1300 is now cut through the drape 110 at the fourth removable core 204 and a hole 1302 is cut through the drape 110 at the ninth removable core 209. Cutting templates 304 (if present) facilitate creation of the holes 1300, 1302 and are then removed. The fourth removable core 204 is separated from the foam layer 112 and removed via the hole 1300, creating a channel 1304 extending through the foam layer 112. The ninth removable core 209 is separated from the foam layer 112 and removed via the hole 1300, creating a channel 212 extending through the foam layer 112. The wound bed 108 is visible through the channels 1304, 212. The wound bed 108 may also be inspected, treated, manipulated, altered, etc. via the channels 1304, 212. Medication or other substance or object may be applied to the wound bed 108 via the channels 1304, 212.

While the dressing 106 is in the configuration shown in FIG. 13, the condition of wound bed 108 may be assessed via channel 1304 and channel 212. Because the channels 1304, 212 are positioned in different locations on the dressing 106, the condition of multiple portions of the wound bed 108 may be assessed. A caregiver may thereby acquire direct information needed to conceive of an updated treatment plan and/or monitor healing progress for the wound bed 108. In some cases, a caregiver may determine that the healing of the wound bed 108 would benefit from the therapeutic properties of one or more of the variety of replacement cores 308. In some cases, the caregiver may determine that a first portion of the wound bed 108 (e.g., visible through the channel 1304) may benefit from a first type of replacement core 308 while a second portion of the wound bed 108 (e.g., visible through the channel 212) may benefit from a second type of replacement core 308. In other cases, the caregiver may determine that the wound bed 108 may benefit from a customized compressibility profile of the dressing 106 that may be created by using replacement cores 308 of various densities to affect how various parts of the foam layer 112 compress under negative pressure. Replacement cores 308 may also be chosen to customize the flow of fluid through the foam layer 112. Various replacement cores 308 may thereby be selected to customize the therapeutic profile of the dressing 106.

Figure 14:
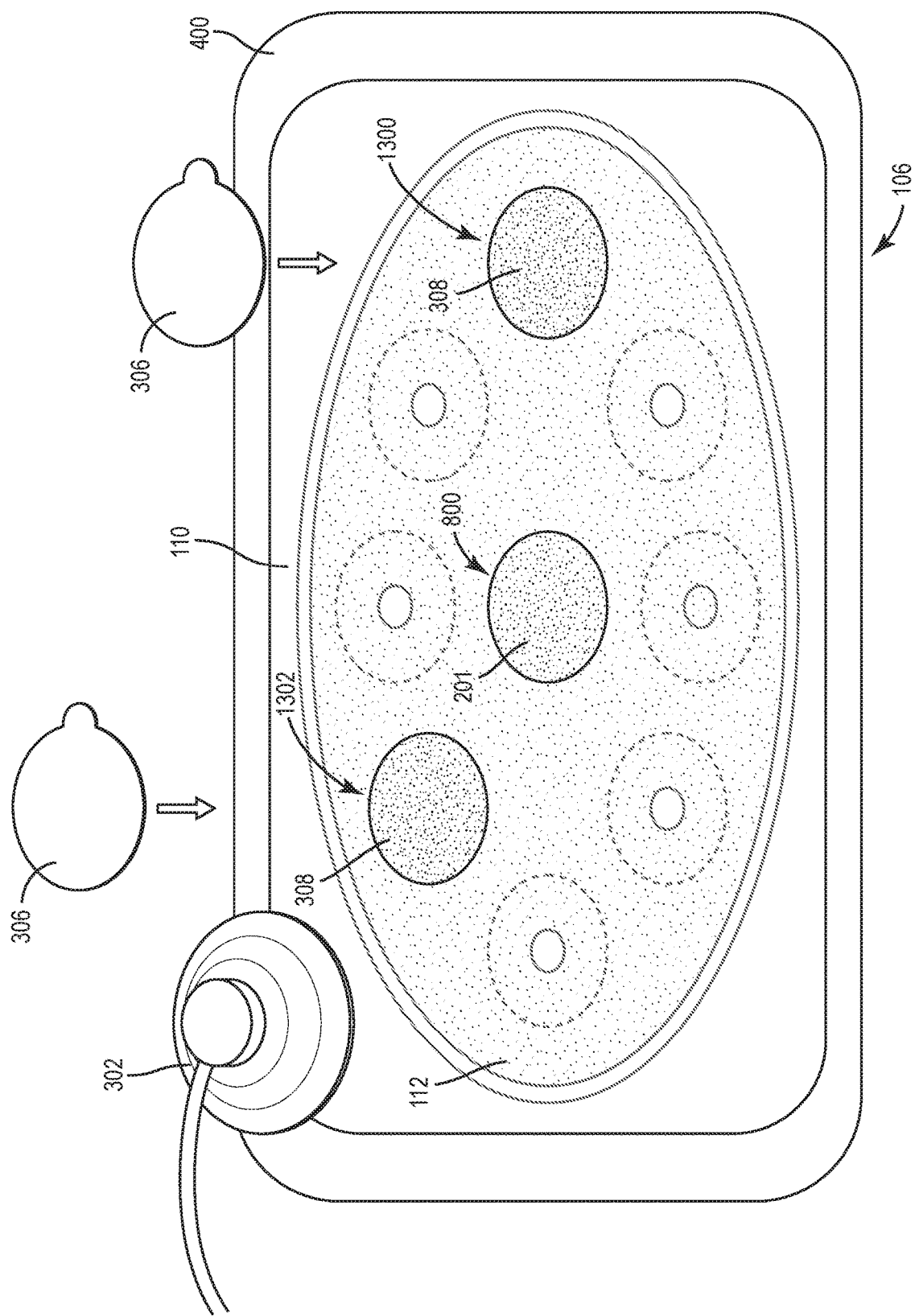
FIG. 14 is an illustration of a tenth step of providing NPWT to the wound bed of FIG. 4 with the dressing kit of FIG. 3, according to an exemplary embodiment.

Referring now to FIG. 14, selected replacement cores 308 are inserted into the channels 1304, 212 to replace the fourth removable core 204 and the ninth removable core 209. The replacement cores 308 are placed adjacent the wound bed 108. As shown in FIG. 14, the foam layer 112 may be understood as including the replacement cores 308 received by the channels 1304, 212. In other words, the foam layer 112 has been customized to include various materials distributed to various portions of the wound bed 108. Patches 306 are retrieved from the dressing kit 300 for use in sealing the holes 1300, 1302, as described with reference to FIG. 15.

Figure 15:
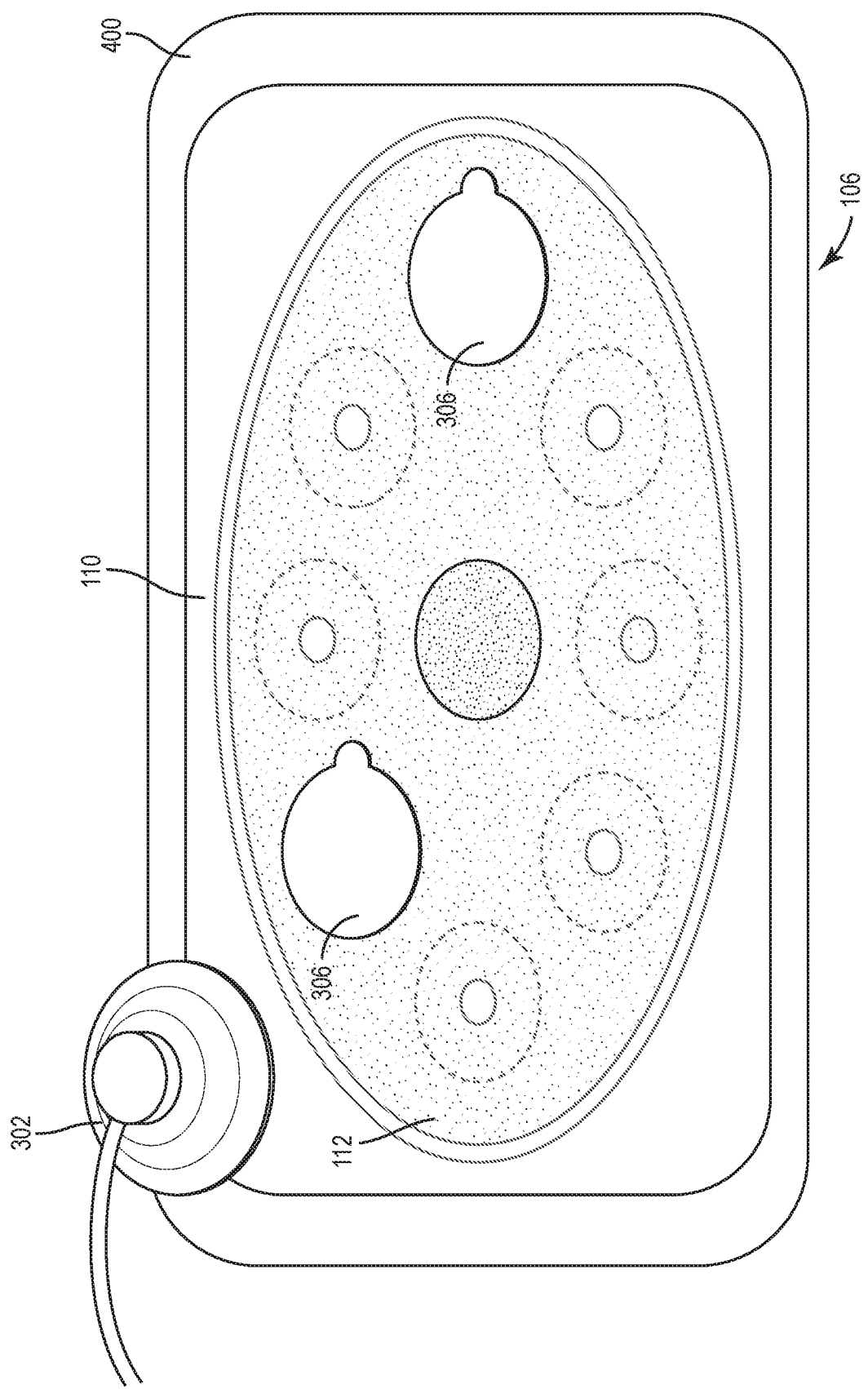
FIG. 15 is an illustration of an eleventh step of providing NPWT to the wound bed of FIG. 4 with the dressing kit of FIG. 3, according to an exemplary embodiment.

Referring now to FIG. 15, a patch 306 is sealed over the hole 1300 and another patch 306 is sealed over the hole 1302. In some embodiments, each patch 306 includes a backing that can be peeled off to reveal an adhesive that binds the patch 306 to the drape 110. The patches 306 can then be placed over the holes 1300, 1302 to substantially prevent fluid from leaking between the external environment and the foam layer 112 (i.e., the replacement cores 308) via the holes 1300, 1302.

Figure 16:
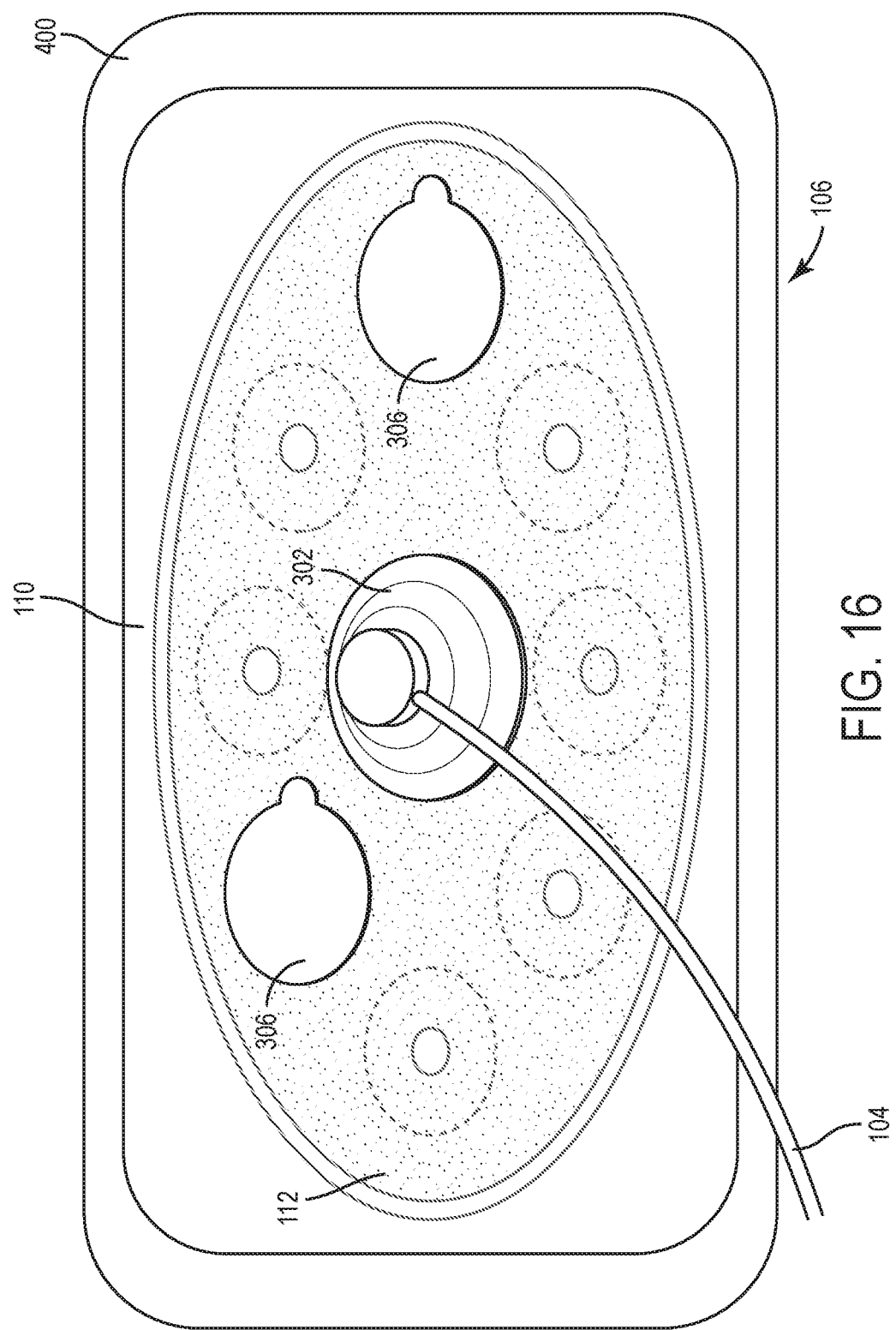
FIG. 16 is an illustration of a twelfth step of providing NPWT to the wound bed of FIG. 4 with the dressing kit of FIG. 3, according to an exemplary embodiment.

Referring now to FIG. 16, the trackpad 302 is resealed to the drape 110 to seal the hole 800 at the position of the first removable core 201. A substantially-airtight volume between the drape 110 and the wound bed 108 is reestablished, with the patches 306 and the trackpad 302 sealing the holes 800, 1300, 1302 made in the drape 110 to access the removable cores 201, 204, 209. The tube 104 is placed in fluid communication with the volume (i.e., with the foam layer 112), and the therapy device 102 operates the pump 114 to establish and maintain a negative pressure at the wound bed 108. NPWT may thereby continue with the replacement cores 308 incorporated into the dressing 106.

The wound bed 108 may be further inspected and the dressing 106 may be further customized following similar steps to those shown in FIGS. 4-16. For example, the channel 212 may be reopened by removing the corresponding patch 306 (e.g., peeling the patch 306 off the dressing 106, cutting a hole through the patch 306) and removing the replacement core 308 inserted into the channel 212. The wound bed 108 may then be inspected. The same replacement core 308 or a different replacement core 308 may then be replaced in the channel 212, and a patch 308 may be resealed over the channel 212. As another example, the sixth removable core 206 may be removed by cutting a hole through the drape 110 at the sixth removable core 206 and extracting the sixth removable core 206 through the hole. This hole may be cut with or without the assistance of a cutting template 304. A replacement core 308 may be inserted and a patch 306 placed over the replacement core 308 to reseal the drape 110.

Although FIGS. 4-16 illustrate an example sequence of steps, it should be understood that the present disclosure contemplates any iteration or combination of the steps of creating one or more holes in the drape 110, removing one or more cores (i.e., removable cores 201-209 and/or replacement cores 308) from the dressing 106, inspecting the wound through one or more channels created by removing the cores, customizing a therapeutic profile of the dressing 106 by inserting cores (removable cores 201-209 and/or replacement cores 308) into the one or more channels, applying patches to reseal the drape 110, and operating a pump 114 to establish a negative pressure at the wound bed 108. The dressing kit 300 thereby facilitates intra-NPWT inspection of the wound bed 108 and intra-NPWT updates to the material composition of the dressing 106, in order to provide an adaptable and customizable dressing for NPWT therapy.

Figure 17:
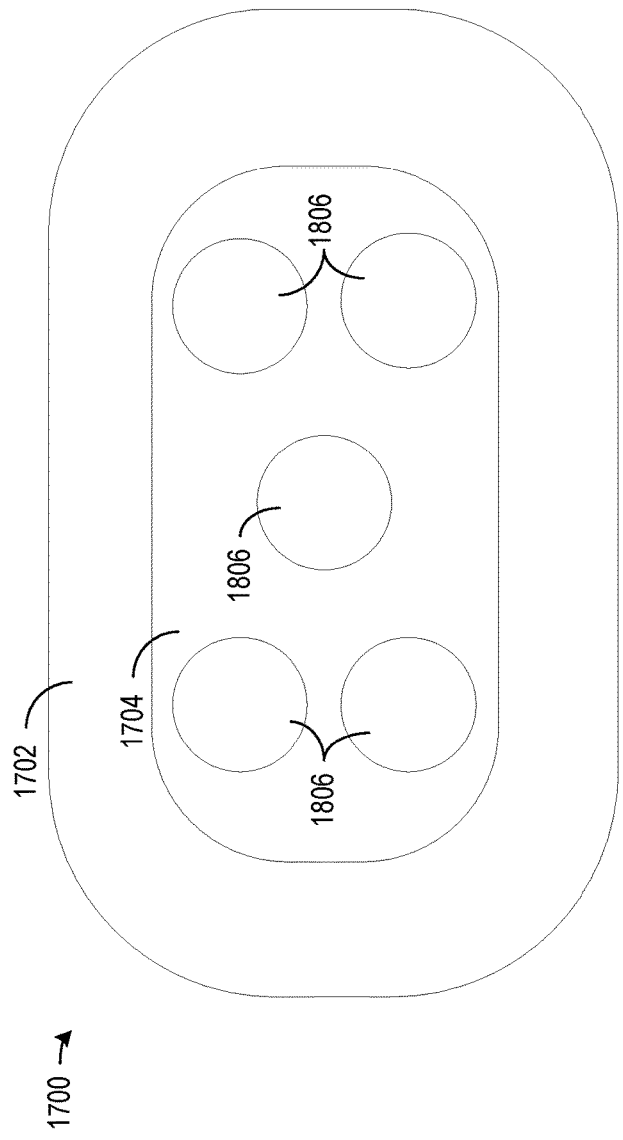
FIG. 17 is a first diagram of an alternative embodiment of the NPWT dressing, according to an exemplary embodiment.
Figure 18:
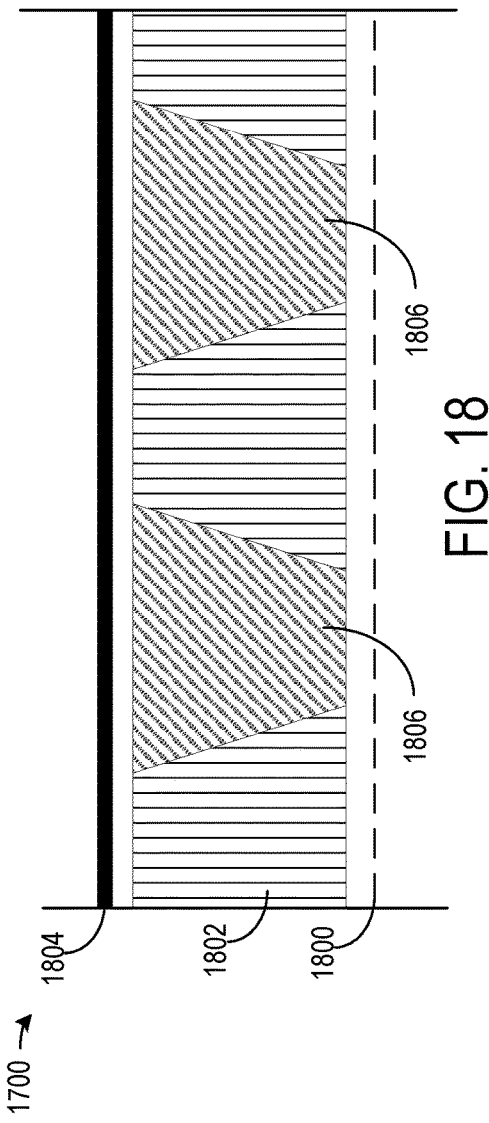
FIG. 18 is a second diagram of an alternative embodiment of the NPWT dressing, according to an exemplary embodiment.

Referring now to FIGS. 17-18, another embodiment of a dressing for use with the NPWT system 100 is shown, according to an exemplary embodiment. FIG. 17 shows a top view of a dressing 1700. FIG. 18 shows a cross-sectional view of the dressing 1700.

The dressing 1700 includes an adhesive border 1702 surrounding a treatment portion 1704. The adhesive border 1702 includes an adhesive configured to adhere the dressing 1700 to a patient with the treatment portion 1704 positioned at a wound bed 108. The adhesive border 1702 may form a substantially airtight seal with the patient's skin (e.g., with the periwound 400) to allow a negative pressure to be created and maintained at the wound bed 108.

The treatment portion 1704 includes a fenestrated film layer 1800 that abuts the wound bed 108 when the dressing 1700 is applied, a foam layer 1802 that abuts the fenestrated film layer 1800, and a drape layer 1804 that abuts the foam layer 1802. The fenestrated film layer 1800 provides a surface that encourages wound healing while allowing air and fluid to flow therethrough. The foam layer 1802 may be manufactured from a polyurethane foam, for example V.A.C.® GranuFoam™ by Acelity. The drape layer 1804 may be substantially impermeable to air and fluid, combining with the adhesive border 1702 to provide a substantially airtight volume at the wound bed 108. The substantially airtight volume includes the foam layer 1802 and the fenestrated film layer 1800. The drape layer 1804 is couplable to a trackpad 302 to allow a negative pressure to be established and maintained at the wound bed 108 by the pump 114 of the therapy device 102. The dressing 1700 may be manufactured and distributed as a unified product (i.e., as opposed to a dressing kit for user-assembly).

The foam layer 1802 includes removable cores 1806. In the embodiment shown in FIG. 17, the foam layer 1802 includes five removable cores 1806. Other embodiments include various other numbers of removable cores 1806. The removable cores 1806 may be arranged on the foam layer 1802 in a variety of arrangements. The removable cores 1806 may be removed and replaced using the approach described above with reference to FIGS. 4-16. The fenestrated film layer 1800 may remain in contact with the wound bed 108 while the removable cores 1806 are removed and replaced.

As shown in FIG. 18, each removable core 1806 has a tapered form (e.g., frustoconical, etc.) such that the surface area of an upper end of the removable core 1806 is greater than the surface area of a lower end of the removable core 1806. That is, the removable cores 1806 are shaped as sub-sections of cones. The tapered form of the removable cores 1806 may facilitate removal and replacement of the removable cores 1806.

As utilized herein, the terms "approximately," "about," "substantially," and similar terms are intended to have a broad meaning in harmony with the common and accepted usage by those of ordinary skill in the art to which the subject matter of this disclosure pertains. It should be understood by those of skill in the art who review this disclosure that these terms are intended to allow a description of certain features described and claimed without restricting the scope of these features to the precise numerical ranges provided. Accordingly, these terms should be interpreted as indicating that insubstantial or inconsequential modifications or alterations of the subject matter described and are considered to be within the scope of the disclosure.

Other arrangements and combinations of the elements described herein and shown in the Figures are also contemplated by the present disclosure. The construction and arrangement of the systems and apparatuses as shown in the various exemplary embodiments are illustrative only. Although only a few embodiments have been described in detail in this disclosure, many modifications are possible (e.g., variations in sizes, dimensions, structures, shapes and proportions of the various elements, values of parameters, mounting arrangements, use of materials, colors, orientations, etc.). For example, the position of elements can be reversed or otherwise varied and the nature or number of discrete elements or positions can be altered or varied. Accordingly, all such modifications are intended to be included within the scope of the present disclosure. Other substitutions, modifications, changes, and omissions can be made in the design, operating conditions and arrangement of the exemplary embodiments without departing from the scope of the present disclosure.

What is claimed is:

1. A dressing, comprising:
   a foam layer;
   a plurality of cores removably attached to the foam layer and extending substantially through the foam layer;
   a plurality of perforations in the foam layer positioned around each of the cores, each of the cores configured to separate from the foam layer at the perforations; and
   a drape sealable over the foam layer and a wound bed, the drape defining a substantially-airtight volume between the drape and the wound bed that contains the foam layer, the drape couplable to a pump operable to create a negative pressure in the substantially-airtight volume;
   wherein each core is substantially removable from the foam layer to reveal a channel through the foam layer.

2. The dressing of claim 1, wherein each core is substantially removable from the foam layer by:
   cutting a hole through the drape at a location of the core; and
   extracting the core from the foam layer through the hole.

3. The dressing of claim 2, further comprising a patch sealable over the hole to reseal the substantially-airtight volume.

4. The dressing of claim 2, further comprising a cutting template configured to be positioned between the drape and the core that facilitates cutting the hole through the drape.

5. The dressing of claim 1, wherein the wound bed is visible through the channel when the core is removed.

6. The dressing of claim 1, wherein the channel is configured to receive a replacement core, the foam layer and the replacement core having one or more differing physical characteristics.

7. A dressing kit, comprising:
   a foam layer with a plurality of removable cores extending therethrough;
   a drape configured to seal the foam layer over a wound bed, the drape allowing a hole to be created therethrough, the hole allowing one of the plurality of removable cores to be removed from the foam layer to create a channel through the foam layer; and
   one or more patches, each patch comprising an adhesive sealable to an exterior surface of the drape over the removable cores to close the hole in the drape.

8. The dressing kit of claim 7, further comprising a variety of replacement cores configured to be received by the channel, each of the variety of replacement cores associated with a different therapeutic benefit.

9. The dressing kit of claim 8, wherein the variety of replacement cores includes one or more of a high-density core having a density higher than the plurality of removable cores, a low-density core having a density lower than the plurality of removable cores, a debridement core, a cleansing core, a silver ion foam core, a hydrophobic core, a hydrophilic core, or a fluid collection core.

10. The dressing kit of claim 7, further comprising one or more cutting templates, each cutting template positionable between one of the plurality of removable cores and the drape to facilitate creation of the hole.

11. The dressing kit of claim 10, wherein each cutting template has a shape that matches a cross-sectional shape of one or more of the plurality of removable cores.

12. The dressing kit of claim 7, further comprising a trackpad couplable to the drape, the trackpad configured to provide fluid communication between the wound bed and a pump operable to create a negative pressure at the wound bed.

13. The dressing kit of claim 8, wherein replacing one or more of the removable cores with one or more of the variety of replacement cores alters a compressibility profile of the foam layer.

14. A method for treating a wound, comprising:
   placing a foam layer on the wound, a plurality of cores extending through the foam layer;
   sealing the foam layer over the wound with a drape;
   cutting a hole through the drape;
   removing a first core of the plurality of cores through the hole to create a channel through the foam layer to the wound;
   placing the first core or a replacement core in the channel; and
   adhering a patch to an exterior surface of the drape to seal the hole and the first core or the replacement core.

15. The method of claim 14, further comprising coupling a trackpad to the drape, the trackpad configured to provide fluid communication between the foam layer and a pump, the pump configured to create a negative pressure at the foam layer.

16. The method of claim 14, the replacement core having one or more material properties different than the first core.

17. The method of claim 14, wherein the replacement core comprises a high-density core having a density higher than the first core, a low-density core having a density lower than the first core, a debridement core, a cleansing core, a sliver foam core, a hydrophobic core, a hydrophilic core, or a fluid collection core.

18. The method of claim 14, further comprising targeting a therapy to a portion of the wound visible through the channel by:
   selecting the replacement core from a kit of replacement cores having various therapeutic benefits, the replacement core configured to provide the therapy; and
   placing the replacement core in the channel proximate the portion.

19. The method of claim 14, further comprising:
   cutting a plurality of additional holes through the drape;
   removing additional cores of the plurality of cores through the plurality of additional holes;
   replacing the additional cores with a plurality of replacement cores; and
   resealing the additional holes with a plurality of patches.

20. The method of claim 19, wherein the plurality of replacement cores has a variety of densities, the method further comprising customizing a compressibility profile of the foam layer by arranging the plurality of replacement cores to provide the foam layer with a variable density.

* * * * *